United States Patent
Ervin

(10) Patent No.: US 7,996,106 B2
(45) Date of Patent: Aug. 9, 2011

(54) METHOD, SYSTEM AND APPARATUS FOR CONTROLLING PATIENT ACCESS TO MEDICAMENTS

(75) Inventor: Matthew J. Ervin, Mount Vernon, NY (US)

(73) Assignee: Medicasafe, Inc., New York, NY (US)

( * ) Notice: Subject to any disclaimer, the term of this patent is extended or adjusted under 35 U.S.C. 154(b) by 884 days.

(21) Appl. No.: 11/892,612

(22) Filed: Aug. 24, 2007

(65) Prior Publication Data
US 2008/0228317 A1 Sep. 18, 2008

Related U.S. Application Data

(60) Provisional application No. 60/906,525, filed on Mar. 13, 2007.

(51) Int. Cl.
*G06F 17/00* (2006.01)
(52) U.S. Cl. ............ 700/237; 700/240; 700/241
(58) Field of Classification Search .......... 700/237, 700/240, 241
See application file for complete search history.

(56) References Cited

U.S. PATENT DOCUMENTS

| | | | |
|---|---|---|---|
| 5,036,462 A * | 7/1991 | Kaufman et al. | 700/240 |
| 5,562,232 A * | 10/1996 | Pearson | 221/7 |
| 6,330,491 B1 | 12/2001 | Lion | |
| 6,438,451 B1 * | 8/2002 | Lion | 700/237 |
| 6,892,941 B2 * | 5/2005 | Rosenblum | 700/237 |
| 6,973,371 B1 * | 12/2005 | Benouali | 700/244 |
| 7,178,688 B2 * | 2/2007 | Naufel et al. | 221/93 |
| 7,366,675 B1 * | 4/2008 | Walker et al. | 705/2 |
| 7,743,923 B2 * | 6/2010 | Conley | 221/1 |
| 2004/0158349 A1 | 8/2004 | Bonney et al. | |
| 2006/0071011 A1 | 4/2006 | Varvarelis et al. | |
| 2006/0155607 A1 | 7/2006 | Bahir | |
| 2006/0218015 A1 | 9/2006 | Walker et al. | |

FOREIGN PATENT DOCUMENTS

| | | |
|---|---|---|
| EP | 1316929 | 6/2003 |
| WO | WO-0209001 | 1/2002 |
| WO | WO-02078594 | 10/2002 |
| WO | WO-2006070359 | 7/2006 |
| WO | WO-2006106405 | 10/2006 |

* cited by examiner

Primary Examiner — Timothy Waggoner
(74) Attorney, Agent, or Firm — Stroock & Stroock & Lavan LLP

(57) ABSTRACT

A method, system and apparatus for controlling patient access to medicaments are disclosed. A method, system and apparatus can include an interfacing system such as an IVR system that can receive identifying data from a user of a medicament dispensing device. The interfacing system can also communicate limited-use access authorization data to the user via a communicative intermediary. The limited-use access authorization data enables the dispensing device to dispense a medicament up to a certain limit in response to entering the access authorization data into the dispensing device. The dispensing device may not be connected to a network, but is capable of computing and storing a limited-use access authorization data as well as validating an inputted access authorization data.

32 Claims, 8 Drawing Sheets

METHOD, SYSTEM AND APPARATUS FOR CONTROLLING PATIENT ACCESS TO MEDICAMENTS

CROSS REFERENCE TO RELATED APPLICATIONS

This application claims priority, under 35 U.S.C. §119(e), to U.S. Provisional Patent Application Ser. No. 60/906,525, filed Mar. 13, 2007, the disclosure of which is incorporated by reference herein in its entirety.

BACKGROUND

Various medications are prescribed to combat illnesses and ailments. The use of prescribed medication, usually provided in pill form, has increased as medical science has progressed. Likewise, advancements in medical science have increased the selection, application and potency of prescription medications. Moreover, various diseases, conditions and illnesses that once required or allowed a patient to opt for hospitalization are now commonly treated on an out-patient basis through a prescribed medication regimen.

For the above reasons and more, many medications including many drugs in pill form are now regularly self-administered under little to no supervision. Self-administration of medication increases the possibility that a patient will fail to comply with directions regarding such things as dosage and timing. Non-compliance can greatly diminish the effectiveness of the treatment as well as increase the likelihood of harm to the patient, neither of which are desirable. Further, non-compliance can increase healthcare costs and consume healthcare resources that could be allocated elsewhere but for the non-compliance.

Non-compliance includes such things as underdosing, overdosing, abuse and dependency, which typically affect a patient's overall health and, in many cases, can be life-threatening. Non-compliance does not only directly affect the patient's health and economical wellbeing, but can indirectly affect the health and economical wellbeing of family, friends and society as a whole. Overall, non-compliance on a national and worldwide scale is costly.

Underdosing and overdosing often occur by simple mistake or neglect, particularly, when a patient is required to self-administer a complex regimen of medications. Nevertheless, both underdosing and overdosing can be intentional. For example, underdosing may be attempted by a patient to lower healthcare costs. Overdosing may be an unsound attempt to increase the therapeutic effectiveness of the medication or to cause self-inflicted harm as well as be the result of abuse or dependency.

Abuse such as recreational use or unauthorized distribution is always a societal concern. Often abuse is interrelated to dependency. The risk of dependency is of particular concern when the prescribed medication is known to be habit-forming or outright addictive. Although the risk of dependency is particularly acute when the patient is known to be high-risk (i.e. susceptible to abuse and addiction), dependency remains a risk with all patients.

Thus, the risks associated with non-compliance are a real concern for doctors, pharmacists and manufacturers, among others. As a result, doctors often under-prescribe certain medications, thereby, lessening the benefits of the medication. Doctors and other healthcare professionals are also forced to make dependency risk determinations about their patients, which can put the patient and the doctor in an uncomfortable, possibly, compromising situation.

SUMMARY

According to at least one embodiment, a method of controlling access to medicaments in a medicament dispensing device can include receiving identifying data from a user and evaluating whether or not to grant access to the medicaments based on the identifying data received. If a decision is made to grant access, then limited-use access authorization data can be determined where the limited-use access authorization data enables the dispensing device to dispense the medicaments up to a certain limit. The limited-use access authorization data can be communicated to the user.

In another exemplary embodiment, a system for controlling access to medicaments can include an interfacing system configured to interface with a communicative intermediary and a dispensing device for securely dispensing the medicaments. The dispensing device can be capable of providing limited access to the medicaments in response to valid access authorization data. The access authorization data can be independently calculatable by both the device and the interfacing system and can be of limited use. Thus, limited access to the medicaments can be granted via communication of the valid limited-use authorization data from the interfacing system to a user via a communicative intermediary.

In yet another exemplary embodiment, a method of controlling access to medicaments can include a means for inputting identifying data, a means for authorizing the inputted identifying data and a means for outputting access authorization data.

BRIEF DESCRIPTION OF THE FIGURES

Advantages of embodiments of the present invention will be apparent from the following detailed description of the exemplary embodiments thereof, which description should be considered in conjunction with the accompanying drawings in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

Figure 1:
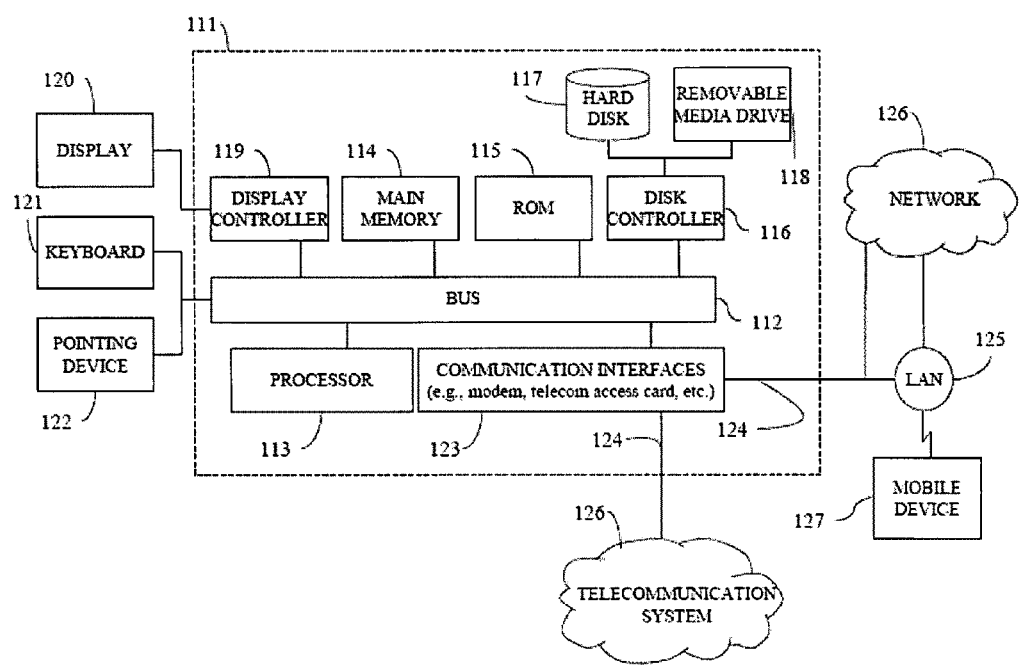
FIG. 1 is an exemplary diagram of a computer network.

FIG. 1 illustrates a computer system 111 upon which an embodiment of the present invention may be implemented. The computer system 111 includes a bus 112 or other communication mechanism for communicating information, and a processor 113 coupled with the bus 112 for processing the information. The computer system 111 also includes a main memory 114, such as a random access memory (RAM) or other dynamic storage device (e.g., dynamic RAM (DRAM), static RAM (SRAM), and synchronous DRAM (SDRAM)), coupled to the bus 112 for storing information and instructions to be executed by processor 113. In addition, the main memory 114 may be used for storing temporary variables or other intermediate information during the execution of instructions by the processor 113. The computer system 111 further includes a read only memory (ROM) 115 or other static storage device (e.g., programmable ROM (PROM), erasable PROM (EPROM), and electrically erasable PROM (EEPROM)) coupled to the bus 112 for storing static information and instructions for the processor 113.

The computer system 111 also includes a disk controller 116 coupled to the bus 112 to control one or more storage devices for storing information and instructions, such as a magnetic hard disk 117, and a removable media drive 118 (e.g., floppy disk drive, read-only compact disc drive, read/write compact disc drive, compact disc jukebox, tape drive, and removable magneto-optical drive). The storage devices may be added to the computer system 111 using an appropriate device interface (e.g., small computer system interface (SCSI), integrated device electronics (IDE), enhanced-IDE (E-IDE), direct memory access (DMA), or ultra-DMA).

Further, exemplary embodiments include or incorporate at least one database which may store software, descriptive data, system data, digital images and any other data item required by the other components necessary to effectuate any embodiment of the present system and method known to one having ordinary skill in the art. The databases may be provided, for example, as a database management system (DBMS), a relational database management system (e.g., DB2, Oracle, SQL Server, My SQL, ACCESS, etc.), an object-oriented database management system (ODBMS), a file system or another conventional database package as a few non-limiting examples. The databases can be accessed via a Structure Query Language (SQL) or other tools known to one having skill in the art.

The computer system 111 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 111 may also include a display controller 119 coupled to the bus 112 to control a display 120, such as a cathode ray tube (CRT), liquid crystal display (LCD) or any other type of display, for displaying information to a computer user. The computer system includes input devices, such as a keyboard 121 and a pointing device 122, for interacting with a computer user and providing information to the processor 113. Additionally, a touch screen could be employed in conjunction with display 120. The pointing device 122, for example, may be a mouse, a trackball, or a pointing stick for communicating direction information and command selections to the processor 113 and for controlling cursor movement on the display 120. In addition, a printer may provide printed listings of data stored and/or generated by the computer system 111.

The computer system 111 performs a portion or all of the processing steps of the invention in response to the processor 113 executing one or more sequences of one or more instructions contained in a memory, such as the main memory 114. Such instructions may be read into the main memory 114 from another computer readable medium, such as a hard disk 117 or a removable media drive 118. One or more processors in a multi-processing arrangement may also be employed to execute the sequences of instructions contained in main memory 114. In alternative embodiments, hard-wired circuitry may be used in place of or in combination with software instructions. Thus, embodiments are not limited to any specific combination of hardware circuitry and software.

As stated above, the computer system 111 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 111, for driving a device or devices for implementing the invention, and for enabling the computer system 111 to interact with a human user. Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 113 for execution. A computer readable medium may take many forms, including but not limited to, non-volatile media, volatile media, and transmission media. Non-volatile media includes, for example, optical, magnetic disks, and magneto-optical disks, such as the hard disk 117 or the removable media drive 118. Volatile media includes dynamic memory, such as the main memory 114. Transmission media includes coaxial cables, copper wire and fiber optics, including the wires that make up the bus 112. Transmission media also may also take the form of acoustic or light waves, such as those generated during radio wave and infrared data communications.

Various forms of computer readable media may be involved in carrying out one or more sequences of one or more instructions to processor 113 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 111 may receive the data on the telephone line and use an infrared transmitter to convert the data to an infrared signal. An infrared detector coupled to the bus 112 can receive the data carried in the infrared signal and place the data on the bus 112. The bus 112 carries the data to the main memory 114, from which the processor 113 retrieves and executes the instructions. The instructions received by the main memory 114 may optionally be stored on storage device 117 or 118 either before or after execution by processor 113.

The computer system 111 also includes at least one communication interface 123 (e.g. modem, telecom access card, etc) coupled to the bus 112. A communication interface 123 may provide a two-way data communication coupling to a network link 124 that is connected to, for example, a local area network (LAN) 125, or to another communications network 126 such as the Internet. The communication interface 123 may also include or serve as a telecom access device (e.g. if the communication interface is a telecom board), thus enabling the computer to act as an IVR (Interactive Voice Response) system. One non-limiting example of such telecom access hardware is commercially available from Dialogic, for example the Dialogic 480JCT board. Further, the communication interface 123 may be a network interface card to attach to any packet switched LAN. As another example, the communication interfaces 123 may be an asymmetrical digital subscriber line (ADSL) card, an integrated services digital network (ISDN) card or a modem to provide a data communication connection to a corresponding type of communications line. Wireless links may also be implemented. In any such implementation, the communication interfaces 123 may send and receive electrical, electromagnetic or optical signals that carry digital data streams representing various types of information.

The network link 124 typically provides data communication through one or more networks to other data or telecom devices. For example, the network link 124 may provide a connection to another computer or remotely located presentation device through a local network 125 (e.g., a LAN) or through equipment operated by a service provider, which provides communication services through a communications network 126. In preferred embodiments, the local network 124 and the communications network 126 preferably use electrical, electromagnetic, or optical signals that carry digital data streams. The signals through the various networks and the signals on the network link 124 and through the communication interface 123, which carry the digital data to and from the computer system 111, are exemplary forms of carrier waves transporting the information. The computer system 111 can transmit and receive data, including program code, through the network(s) 125 and 126, the network link 124 and the communication interface 123. Moreover, the network link 124 may provide a connection through a LAN 125 to a mobile device 127 such as a personal digital assistant (PDA) laptop computer, or cellular telephone. The LAN communications network 125 and the communications network 126 both use electrical, electromagnetic or optical signals that carry digital data streams. The signals through the various networks and the signals on the network link 124 and through the communication interface 123, which carry the digital data to and from the system 111, are exemplary forms of carrier waves transporting the information. The processor system 111 can transmit notifications and receive data, including program code, through the network(s), the network link 124 and the communication interface 123.

The exemplary embodiments below may use Interactive Voice Response (IVR) systems. IVR systems may be computing devices which can: answer phone calls; play audio to the caller during a phone call, such as "Please enter your ID number"; and accept input from the caller, for example, via touchtone input or speech input and the like where the caller operates a telephone to signal to the IVR system. By playing audio to a caller and accepting input from the caller, the IVR system conducts a dialog.

Current IVR systems are computers that communicate with phone callers via a wide variety of telecom transmission protocols. That telecom protocol may or may not require that the computer contain a special physical telecom access card, similar to a modem, for connecting to telecom systems and communicating audio via a telecom transmission protocol. Some new digital protocols, such as the Voice over Internet Protocol (VoIP), do not require a special additional modem-like communication subsystem, but may have a communication device that can access a data network (a data card) and may use a program to control VoIP telecom calls. More traditional telephony systems and protocols typically are connected to and controlled by commercially available telecom access cards.

Telecom access cards are specifically designed to enable the computer to connect to a telecom system and contain means to allow the computer to programmatically control a dialog with one or more human beings on the other end of telecommunications connections (i.e., during phone calls). Telecom cards are commercially available such that, when installed in a computer, the computer can connect to and control voice calls over a variety of telecom protocols, including: analog lines, TDM digital lines, ISDN digital lines, Voice over IP lines, etc. Thus, exemplary embodiments of the below invention may use any of the telecom protocols and configurations described above.

In general, FIGS. 2-8 are directed to aspects of at least one exemplary embodiment of a method, system and apparatus for administering medicaments to patients where the medicaments are dispensed in a controlled fashion from a dispensing device. Although many steps are described as being performed by computer logic, a person of ordinary skill in the art will understand that one or more of these steps can be performed by a human being. For example, a human being can answer a phone call from a user, request identifying data, determining whether authorization to a dispensing device is advisable, relay access authorization data to the user for accessing medicaments housed in a dispensing device and the like.

According to at least one embodiment, a method and system of controlling access to medicaments can control the communication of limited-use access authorization data so as to serve as a key and proxy for controlling and tracking access to medicaments in a drug dispensing device. The dispensing device can, in turn, utilize limited-use access authorization data to control access to medicaments. Embodiments can include using a drug dispensing device that can require limited-use access authorization data (e.g., a single-use passcode) to gain access to the medicaments.

The term "access authorization data" is used throughout and passcodes are but one example of such data. Valid passcodes are used in the exemplary embodiments to indicate to the drug dispensing device that access to some amount of medicaments has been authorized.

An important aspect of at least one exemplary embodiment can be considered to be the use of controlled communication of limited-use access authorization data where such access authorization data (a non-limiting example being a passcode) can then be used to enable limited access to medicaments in a drug dispensing device. Access to medicaments can be granted for limited use (e.g., the drug dispensing device only dispenses a certain quantity and/or dispenses over a certain period of time during which the passcode is valid) and at some point the access authorization data can expire. Thereafter, use of that access authorization data can fail to facilitate access to the medicaments in the drug dispensing device.

The access authorization data can be made to expire for any number of reasons such as if the data is used too often within a limited period of time. Once the access authorization data expires and is no longer valid, a user seeking access to further medicaments can seek new access authorization data (e.g. a new passcode) from an external resource (e.g. an external interfacing server via a communicative intermediary). If new access authorization data is not sought, the user can be left without the ability to access the medicaments within the drug dispensing device.

New and valid access authorization data can be provided if the logic of the system controlling communication of the access authorization data deems it proper for the user to gain access to the medicaments at that time. Typically, this would occur if the user can be properly authenticated and if the time at which the user is seeking access is deemed appropriate given the prescribed medicament regimen.

In one exemplary embodiment, the control of communicating valid access authorization data can be achieved by requiring a person (typically the user of the medicaments) to input identifying data to an interfacing server via a communicative intermediary. The interfacing server can then respond via the communicative intermediary with access authorization data if the server and a database as well as logic controlling the server enable the interfacing server to communicate the information needed for accessing the medicaments to the person associated with the identifying data. The identifying data can include one or more items such as a user name, a device identification number, a treatment identification number, a password, and similar data known to one having ordinary skill in the art. Supplemental data collected along with the identifying data could include information displayed on the device such as a status code that can be used to derive further information about the quantity and/or pattern of access to the medicaments during the intervening time since the last communication with the user, A determination of whether access authorization data should be communicated to the user can be controlled by a program and the program can incorporate any algorithm/logic conceived to decide whether or not access should be authorized. Medical considerations that may be considered when conceiving this algorithm include concerns that the patient may be seeking medicament access too frequently and thus may be exhibiting signs of drug addiction, and therefore medicament access should be curtailed. Also, the patient may not be taking the medicament at the right time to maximize the effectiveness of the medicament and access authorization data can be withheld until the appropriate time. The inputs to the algorithm could include data about when the user has sought access to medicaments in the past. At least one exemplary embodiment described herein assumes that the time of dispensing is close to the time of the last communication of valid access authorization data. Alternatively, the dispensing device can be programmed by one with ordinary skill in the art to log the times at which medicaments were accessed in the device. This log, or the most relevant information in this log, can be communicated by the user during the session interval when the user is communicating other identifying information. It would be possible for one with skill in the art to enable the dispenser to track data about when medicaments were removed from the dispenser, and data about this medicament access could be encoded into information that could be communicated by the user, such as a status code. As one non-limiting example, if the dispensing device is programmed to limit usage to no more than three pills during a 48 hour period, the status code for such as 48 hour period could be designed as three 2-digit numbers conjoined, each 2-digit number indicating the hour at which a medicament was dispensed during that 48 hour window. Status code 04 14 36 would indicate that pills were dispensed at hours 4, 14, and 36, while 05 05 00 would indicate that two pills were dispensed during hour 5 and none thereafter. This type of device information, including device status and dispensing history, could be requested during any session wherein the user seeks additional access authorization code data. Any one skilled at the art could conceive of a variety of information that the dispensing device could log, could conceive of protocols for resetting the log with the input of new access authorization data, and could conceive similar protocols for tracking and communicating log files known to one with ordinary skill in the art. All of this information could be communicated along with identifying data.

In at least one exemplary embodiment, the algorithm implemented can check to see if sufficient time has passed since the last access authorization data was supplied. Such a relatively simple algorithm can be useful in controlling access to an addictive medicament, but the simplicity of this exemplary algorithm is not intended to be limiting.

In addition to controlling access to medicaments, embodiments can also serve as a practical mechanism for tracking access to those medicaments and reminding users to take medication if it can be inferred that that have not done so. The user's action to seek access authorization data can be considered a proxy for the actual consumption of medicaments and thus data about the user's actions or lack of actions in seeking medicament access can be medically useful. If the user fails to seek access authorization data at the time expected, this lack of action can be useful data that can employ a reminder system that contacts the user when they are not following a treatment regimen in an appropriate manner. Thus, exemplary embodiment can remind the user to take the medicament during a prescribed time.

Figure 2:
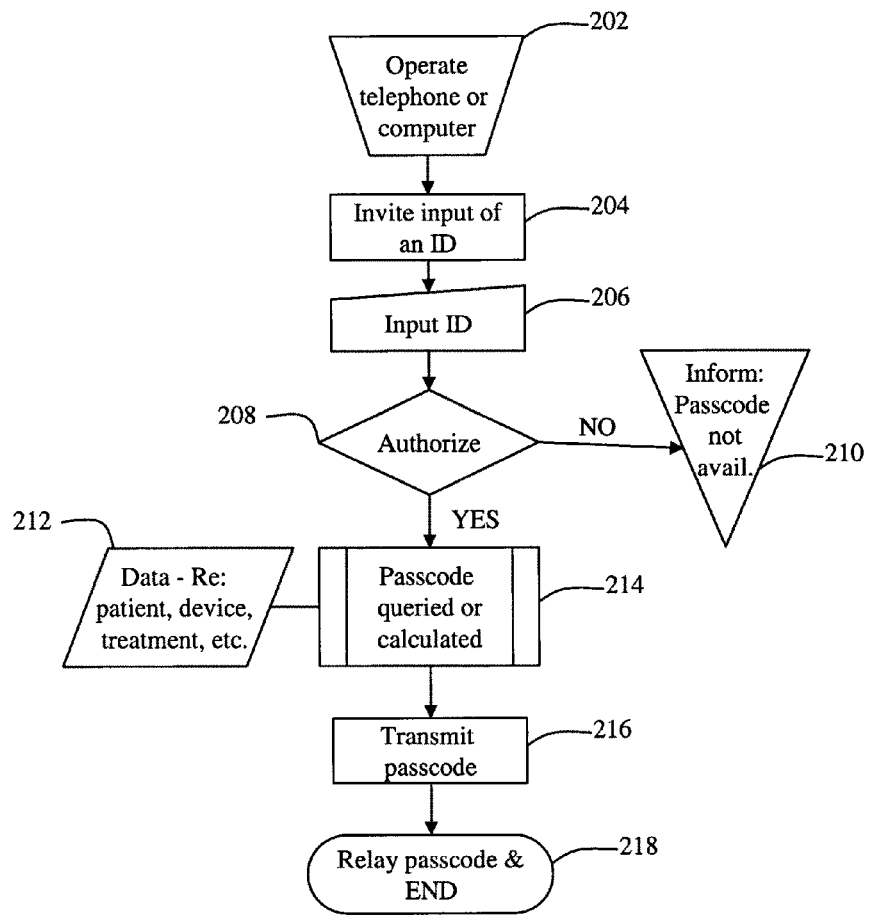
FIG. 2 is a flowchart showing an exemplary process for providing an access authorization data via an interfacing system.

Referring to FIG. 2, a process for accessing a medicament (or predetermined dosage quantity thereof) where a patient can receive access authorization data such as a passcode or password for operating a medicament dispensing device is shown in accordance with at least one exemplary embodiment of the present invention. In at least one exemplary embodiment, the access authorization data can be limited-use access authorization data such as single-use (i.e. "one-time") access authorization data. For instance, single-use access authorization data (a species of limited-use access authorization data) can require a patient to request subsequent single-use access authorization data after the current single-use access authorization data has expired, for example, through a one-time use with the dispensing device and/or through the expiration of the designated time period for use.

Limited-use access can describe access to a certain quantity of medicaments (or dosages thereof) or can describe access to any number of medicaments over a range of time. Also, limited-use access can describe access to a certain quantity over a certain period of time.

As such, limited-use access authorization data is intended to be broadly interpreted as information that can be used to provide access to medicaments based on limiting criteria. Limited-use access authorization data can provide access to a certain quantity of doses of a medicament or can provide access to medicaments over a certain period of time and any combination thereof (e.g., a limited-use passcode can be used up to three times during the next forty-eight hour period and thereafter the passcode will expire). After the limit of use has been reached, the limited-use access authorization data will no longer enable access to medicaments.

Thus, the process shown in FIG. 2 can be repeated each time a patient requests access authorization data for dispensing a medicament and limited-use access authorization data can be provided each time that it is determined to be medically advisable to provide such access authorization data. Exemplary embodiments are sometimes described herein with reference to single-use access authorization data such as a single-use passcode. This is intended to be merely illustrative and not limiting as one of ordinary skill in the art will appreciate that limited-use access authorization data that can allow access to a dosage of medicaments any arbitrary number of times and/or over a predetermined time period.

Exemplary embodiments making reference to single-use access authorization data can also provide limited-use access to any arbitrary quantity of medicaments, open access to medicaments over any arbitrary quantity of time or any quantity over any period of time as will be appreciated by one having ordinary skill in the art. In other words, exemplary embodiments referring to single-use access authorization data can make use of limited-use access authorization data to also provide access to two or more doses of medicaments. In effect, all references herein to single-use access authorization data can be broadened and generalized as limited-use access authorization date.

Still referring to FIG. 2, at step 202, a patient (or a person acting on behalf thereof) can operate a communicative intermediary such as a telephone and like devices having telephone functionality to interface with an interfacing system (e.g., a "remote master system") such as an IVR system. Alternatively, a patient can operate a personal computing device such as a computer having webpage browsing capability to view a webpage requested from a web server that provides a means for inputting identifying data for the patient such as an identification number for the dispensing device (which may also function as a patient identification number or be associated therewith), as shown in step 204. Other non-limiting examples of identifying data may be a username and password selected to correspond with a device identification number, a status code on the device, etc. Moreover, in web-based embodiments, a secured Internet connection may be used, as is well known in the art. In other embodiments, the communicative intermediary can be a device with text messaging functionality and the interfacing system can be one that can process text messages as one more non-limiting example. For example, a patient can transmit (i.e. "text") identifying data to a short code (e.g., five-digit short code as is known in the art) and can be supplied access authorization data if it is deemed medically advisable at the time. Other interfacing implementations will be appreciated by one having ordinary skill in or the art.

At step 204, the communicative intermediary can act to invite a patient to input the identifying data. For example, embodiments having an IVR system can initiate a dialog and make an audio request through a telephone such as: "Please enter your identification number," or "Please enter your device ID number" and the like. Similarly, web-based embodiments can invite a patient to input the identifying data by providing a webpage having a portion for inputting the identifying data. For instance, a webpage provided in response to a patient operating a computing device and requesting the webpage can have a graphical user interface (GUI) widget such as a textbox for entering the identifying data.

In at least one exemplary embodiment, identifying data can be a device ID number. That device can be associated in a database with a certain active patient and a certain active treatment regimen. If the device ID number is the identifying data, then a database (described below) can store an association between the device ID and the patient in possession of that device, information about the medicaments in that device, information about the treatment regimen associated with that treatment and the like.

Nevertheless, identifying data can be any information that enables identification of the patient and thus can guide an algorithm for determining when access authorization data should be allowed to be delivered to the user. Identifying information can also be supplemented by additional information such as status information (e.g. a status code) for the dispensing device, which could include information about the quantity and times at which medicaments were dispensed from the device. And identifying data could also be supplemented by a question and answer dialogue, where the user responds with information that could be medically useful, such as information about pain levels, symptoms, etc.

After a patient responds to the invite by inputting identifying data at step 206, the inputted identifying data can be received at the interfacing computer system. At step 208, the interfacing computer system can request authorization from a storage server system (i.e. which may be referred to as a "master medical system"), which may be a database system having a database storing (and associating) data 212 such as patient biographical data, device data including device identification data and device status data, medical/treatment data pertaining to patients and their prescribed medicament regimens, access authorization data (including, e.g., passcodes, passcode algorithms and the like) and the like known to one having ordinary skill in the art (see, e.g., FIG. 4). As one non-limiting example, the database can be a relational database.

Notably, the interfacing and storage systems can be viewed as integral parts of an authorizing system including both operatively connected in accordance with at least one exemplary embodiment. The interfacing and storage systems can be implemented on a single computer, a central computer system or distributed.

In at least one exemplary embodiment, the interfacing server can collect identifying information from the caller and transmit that data to the storage system. The storage system can process the identifying data, which can be the device identification number, and can execute algorithms to determine whether it is medically advisable to provide a medicament (or predetermined dosage quantity thereof) to the patient associated with the identifying data based on, for example, the treatment data stored within the storage system (e.g., a database thereof) and decision logic configured to process such data.

As will be readily understood by one having ordinary skill in the art, the determination of whether it is medically advisable to provide a medicament can be based on the timing and dosage criteria of the treatment regimen prescribed for the medicament in conjunction with the timing of the last dosage requested by the patient. Such a decision can factor in data such as the last and previous outputs of access authorization data to the patient, which can be recorded within the storage system, and any other device status information or patient information reported during the dialogue with the user. In the absence of detailed device status data, outputs of access authorization data can be considered evidence that the patient actually received their medicament dosage proximate the time the access authorization was requested. Overall, the storage system can be used to track a patient's compliance with the prescribed treatment regimen as well as track various other indicators related to a patient's health.

If it is determined to be medically advisable to deny the patient access to the medicament, then the storage system can transmit a denial to the interfacing system, alerting it that access authorization data is not available for providing to the patient. At step 210, the interfacing system can alert the patient (or a person acting on behalf thereof) that the access authorization data is not available (or accessible) at this time through the communicate intermediary. For example, an audio message in embodiments having an IVR system can be played alerting of such or, alternatively, in web-based embodiments, a webpage showing that the request for access authorization data has been denied and that the access authorization is not available can be displayed to a user of a computing device.

If it is determined to be medically advisable to provide the patient with access to the medicament according to the decision logic, then the storage system can transmit an authorization to the interfacing system to provide the requested access authorization data, which can be limited-use access authorization data such as a passcode, password, visual ticket and the like known to one having ordinary skill in the art. Upon authorization, the interfacing system can compute or retrieve from the storage system the access authorization data at step 214. For example, the interfacing system can compute or retrieve single-use access authorization data, such as a passcode based on a predetermined algorithm (or any known type of random number generator), for generating seemingly random single-use passcodes.

Alternatively, a password generator can be used as the generator for single-use passwords as one more non-limiting example. Exemplary embodiments described herein will generally be described in reference to passcodes, algorithms and random number generators, which is illustrative and not intended to be limiting as will be appreciated by one having ordinary skill in the art.

Still referring to FIG. 2, for example, a database of the storage system can store the algorithm where the interfacing system can query the algorithm and calculate the passcode. Alternatively, at step 214, the access authorization data itself can be queried from a database on the storage system where sets of access authorization data pertaining to each patient are stored for providing limited-use access authorization data in response to a patient's request. For example, the known results of a calculated passcode pattern for providing single-use passcodes can be stored in the database.

In at least one exemplary embodiment, if the patient fails to seek access authorization data for the dispensing device within a predetermined time period or around a prescribed time, the interfacing system or another system may alert the patient or a contact person (e.g., guardian, caregiver, relative, etc.) of the need to request access authorization data. These alerts can be of any type known to one having ordinary skill in the art including, for example, alerts transmitted through phone calls, text messages, emails and audible and/or visual alarms.

Also, in at least one exemplary embodiment, an alert can be transmitted to other parties including medical professionals such as doctors and pharmacists or their respective staff that a patient has failed to communicate a request for access authorization data for the dispensing device. The transmission to such medical professionals can be made through the storage system or, alternatively, through the interfacing system as well as any other suitable system connected therewith. Likewise, in at least one exemplary embodiment, an alert can be sent to medical professionals or a contact person if the patient is seeking access to a medicament in a pattern determined to be suggestive of addiction, abuse, misuse and the like.

At step 216, the interfacing system can transmit the limited-use access authorization data, which may be single-use access authorization data, to the communicative intermediary. At step 218, the communicative intermediary can relay the access authorization data to the patient (or a person acting on behalf thereof). For example, an audio message in embodiments having an IVR system can be played relaying the access authorization data to the telephone user or, alternatively, in web-based embodiments, a webpage showing the access authorization data can be displayed on the computing device of the user.

In relation to the process of FIG. 2, one exemplary embodiment can include server code implemented to allow an IVR system to interact with a patient and provide, for example, a current passcode.

Exemplary code is provided herein for an exemplary embodiment that uses an IVR system. This exemplary code consists of PHP scripts, a common scripting language widely used by programmers skilled in the art of web programming, and VoiceXML code, a common scripting language widely used by programmers skilled in the art of IVR programming.

For instance, an exemplary code device configured to provide the basic IVR system menu can include:

```
<?php
header("Content-type: text/xml");
echo("<?xml version=\"1.0\"?>");
?>
<vxml version="2.1">
<property name="inputmodes" value="dtmf"/>
<form id="mainmenu">
  <field name="menuchoice">
    <grammar type="application/x-jsgf">1|2|0</grammar>
```

```
<prompt>
    Welcome to the Medica Safe access line.
    To receive a new passcode
    for your Medica Safe, press 1.
        If you would like to be reminded of
        your current passcode again, press 2.
</prompt>
<filled>
    <if cond="menuchoice==0">
    <goto next="#support"/>
    </if>
</filled>
</field>
<subdialog name="result" src="#get_device_id">
    <filled>
        <var name="v_device_id" expr="result.device_id"/>
        <if cond="menuchoice==1">
            <submit next="ms1_request_new_code.php"
                namelist="v_device_id" method="post"/>
        <elseif cond="menuchoice==2"/>
            <submit next="ms1_read_current_code.php"
                namelist="v_device_id" method="post"/>
        </if>
    </filled>
</subdialog>
</form>
<!-- subdialog to get device Id number -->
<form id="get_device_id">
    <field name="device_id" type="digits">
        <prompt>
            Please enter the device ID located on your
            Medica Safe device, followed by the pound sign.
        </prompt>
        <filled>
            <return namelist="device_id"/>
        </filled>
```

```
        </field>
    </form>
<form id="support">
    <field name="waitforsupport" type="digits">
        <grammar type="application/x-jsgf">1|2</grammar>
        <prompt>
The wait to speak with a support person is
approximately 10 minutes.     If all you need to do is get a new passcode
to access pills in your Medica Safe device, we
suggest that you press 1 and we will direct you into the automated
system for new pass codes.     You will be asked one key question,
namely the device number which you will find printed on the back of
your Medica Safe device.     Then the system will give you a valid
passcode if you are currently authorized to take this medication.
At times, callers do not hear their passcode correctly.     If you would
like to have your current passcode repeated, press 2 now.
If you have already received the passcode, or are unable to access you
passcode and suspect there is an error, please feel free to wait on the line
for a live operator."
        </prompt>
        <filled>
          <if cond="waitforsupport==1">
                <goto next="ms1_request_new_code.php"/>
            <elseif cond="waitforsupport==2"/>
                <goto next="ms1_read_current_code.php"/>
            </if>
        </filled>
    </field>
</form>
</vxml>
```

Also, an exemplary code device configured to enable a caller to request a new passcode (where authorization is provided via a storage system having a database) can include:

```
<?php
header("Content-type: text/xml");
echo("<?xml version=\"1.0\"?>");
include_once("lib/dbaccess.php");
db_ms1_connect( )
?>
<vxml version="2.1">
<property name="inputmodes" value="dtmf"/>
<?php
if (isset($_POST["v_device_id"]))
{
        $device_id = $_POST["v_device_id"];
        $query="SELECT * FROM Treatment_Info WHERE (FK_Device_ID =
        '$device_id' AND StillActive = '1')";
        $result = mysql_query($query);
        if (mysql_numrows($result)==0)
        {
                echo <<<END
                <form>
                  <block>
                    <prompt>
                    The system does not recognize that Device ID.
                    You entered <say-as type="acronym">$device_id</say-as>.
You should have entered the device ID
                    printed on your device.
                    The system will now return to the main menu.
                    </prompt>
                    <goto next="ms1_intro.php"/>");
                  </block>
                </form>
END;
        } else {
                $treatment_id = mysql_result($result,0,"Treatment_ID");
                $time_nextaccess = mysql_result($result,0,"Time_NextAccess");
                $minimum_timediff = mysql_result
($result,0,"Minimum_Interval");
                $patient_id = mysql_result ($result,0,"FK_Patient_ID");
                $treatment_type = mysql_result ($result,0,"Treatment_Type");
                $query= "SELECT * FROM Device_Info WHERE (Device_ID =
```

```
'$device_id')";
                $result = mysql_query($query);
                $passcode_rank =
mysql_result($result,0,"Passcode_CurrentRank");
                $old_passcode = mysql_result($result,0,"Passcode_Current");
                $now = Time( );
                if ($now > $time_nextaccess)
                {
                        $result = mysql_query("SELECT * FROM Algorithm1");
                        $num_rows = mysql_num_rows($result);
                        ++$passcode_rank;
                        if (($num_rows)<($passcode_rank))
                        {
                                $passcode_rank=1;
                        }
                        $query= "SELECT * FROM Algorithm1 WHERE (Passcode_Rank =
                                '$passcode_rank')";
                        $result = mysql_query($query);
                        $new_passcode = mysql_result($result,0,"Passcode");
                        $query= "UPDATE Device_Info SET
Passcode_Current='$new_passcode',
                                Passcode_Past = '$old_passcode', Passcode_CurrentRank
='$passcode_rank'
                                WHERE Device_ID = '$device_id' ";
                        $result = mysql_query($query);
                        $query = "INSERT INTO Patient_Sessions
                                (FK_Treatment_ID,FK_Device_ID,FK_Patient_ID,
TimeStamp,StatusCode,
                                Passcode_Given, Passcode_GivenPrevious) VALUES
        ('$treatment_id','$device_id','$patient_id','$now','0','$new_passcode'
,'$old_passcode')";
                        mysql_query($query);
                        $time_nextaccess = ($now + $minimum_timediff);
                        $query= "UPDATE Treatment_Info SET Time_NextAccess
='$time_nextaccess'
                                 WHERE (Treatment_ID = '$treatment_id') ";
                        $result = mysql_query($query);
                        ECHO <<<END
                        <form id="state_passcode">
                          <field name="menuchoice">
                            <grammar type="application/x-jsgf">1|2</grammar>
                                <prompt> Your new passcode is <say-as
type="acronym">$new_passcode</say-as>.
                                Again, your new passcode is   <say-as
type="acronym" >$new_passcode</say-as>.
                                To repeat this information again, press 1.
                                To return to the main menu, press 2.
                                </prompt>
                                <filled>
                                    <if cond="menuchoice==1">
                                        <goto next="#state_passcode"/>
                                        <elseif cond="menuchoice==2"/>
                                        <goto next="ms1_intro.php"/>
                                        </if>
                                </filled>
                            </field>
                        </form>
END;
                } else {
                        $time_required = ($time_nextaccess − $now);
                        $hours_required = floor($time_required/3600);
                        $minutes_required = ((floor($time_required/60))%60);
                         echo <<<END
                        <form id="call_back_when">
                          <field name="menuchoice">
                             <grammar type="application/x-jsgf">1|2</grammar>
                                <prompt> You cannot access a new passcode now.
                                You can get a new passcode in
END;
                        echo ("$hours_required hours and $minutes_required
minutes.");
                         echo <<<END
                        Your last passcode was <say-as
type="acronym">$old_passcode.</say-as>
                                If you have already used that last passcode, it will no
longer work.
                                To repeat, your last passcode was <say-as
```

```
type="acronym">$old_passcode.</say-as>
                        To repeat this information again, press 1.
                        To return to the main menu, press 2.
                        </prompt>
                        <filled>
                                <if cond="menuchoice==1">
                                <goto next="#call_back_when"/>
                                <elseif cond="menuchoice==2"/>
                                <goto next="ms1_intro.php"/>
                                </if>
                        </filled>
                        </field>
                        </form>
END;
                }
        }
} else {
echo <<<END
<form>
   <block>
      <prompt>
         You should have entered your device id,as printed on
         on your device The system will now return to the main menu.
      </prompt>
      <goto next="ms1_intro.php"/>
   </block>
</form>
END;
}
mysql_close( );
?>
</vxml>
```

Moreover, embodiments of the present invention can include an exemplary code device configured to remind a caller of their current passcode if forgotten, which can include:

```
<?php
header("Content-type: text/xml");
echo("<?xml version=\"1.0\"?>");
include_once("lib/dbaccess.php");
db_ms1_connect( )
?>
<vxml version="2.1">
<property name="inputmodes" value="dtmf"/>
<?php
if (isset($_POST["v_device_id"]))
{
        $device_id = $_POST["v_device_id"];
        $query="SELECT * FROM Treatment_Info WHERE (FK_Device_ID =
        '$device_id' AND StillActive = '1')";
        $result = mysql_query($query);
        if (mysql_numrows($result)==0)
        {
                echo <<<END
                <form>
                   <block>
                      <prompt>
                      The system does not recognize that Device ID.
                      You entered <say-as type="acronym"> $device_id </say-as>.
You should have entered the device ID
                         printed on your device.
                         The system will now return to the main menu.
                      </prompt>
                      <goto next="ms1_intro.php"/>");
                   </block>
                </form>
END;
        } else {
                $treatment_id = mysql_result($result,0,"Treatment_ID");
                $time_nextaccess = mysql_result($result,0,"Time_NextAccess");
                $minimum_timediff = mysql_result
```

```
($result,0,"Minimum_Interval");
            $patient_id = mysql_result ($result,0,"FK_Patient_ID");
            $treatment_type = mysql_result ($result,0,"Treatment_Type");
            $query= "SELECT * FROM Device_Info WHERE (Device_ID =
'$device_id')";
            $result = mysql_query($query);
            $passcode_rank =
mysql_result($result,0,"Passcode_CurrentRank");
            $old_passcode = mysql_result($result,0,"Passcode_Current");
            $now = Time( );
            $time_required = ($time_nextaccess - $now);
            if ($time_required <= 0 ) {
                    $time_required=0;
            }
            $hours_required = floor($time_required/3600);
            $minutes_required = ((floor($time_required/60))%60);
            echo <<<END
<form id="call_back_when">
   <field name="menuchoice">
      <grammar type="application/x-jsgf">1|2</grammar>
      <prompt>
            Your last passcode was <say-as
type="acronym">$old_passcode</say-as>.
                    If you have already used that last passcode, it
will no longer work.
                    To repeat, your last passcode was    <say-as
type="acronym">$old_passcode</say-as>.
            You can get a new passcode in
END;
            echo ("$hours_required hours and $minutes_required
minutes.");
            echo <<<END
            To repeat, your last passcode was <say-as
type="acronym">$old_passcode.</say-as>
            To repeat this information again, press 1.
            To return to the main menu, press 2.
               </prompt>
         <filled>
                <if cond="menuchoice==1">
                <goto next="#call_back_when"/>
                <elseif cond="menuchoice==2"/>
                <goto next="ms1_intro.php"/>
                </if>
         </filled>
      </field>
   </form>
END;
    }
} else {
echo <<<END
<form>
   <block>
      <prompt>
         You should have entered your device id,as printed on
         on your device The system will now return to the main menu.
      </prompt>
      <goto next="ms1_intro.php"/>
   </block>
</form>
END;
}
mysql_close( );
?>
</vxml>
```

Figure 3:
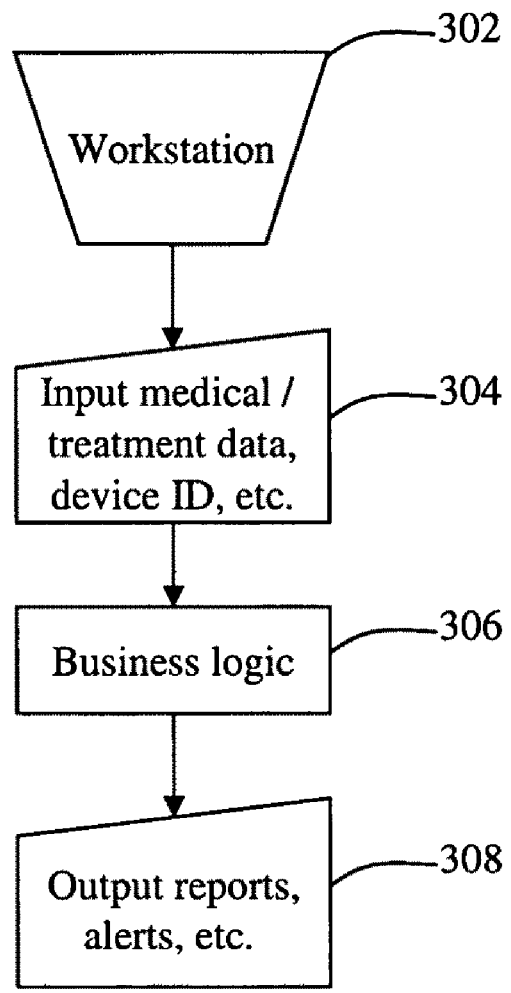
FIG. 3 is a flowchart showing an exemplary process for a storage system.

Now referring to FIG. 3, a process for inputting data, such as patient biographical data, device data including device identification data, medical/treatment data pertaining to patients and their prescribed medicament regimens and the like, into a storage system (i.e. the medical master system) is shown in accordance with at least one exemplary embodiment of the present invention. At step 302, an operator can operate a terminal for a computing device for inputting such data into the storage system while, for example, at a workstation. The storage system can be remote and remotely accessible from the client computing device through a network such as the Internet.

The operator of such a computing device is envisioned, in accordance with at least one exemplary embodiment, to be an administrator for a medical provider. For example, the medical provider can be a hospital, a doctor's office, a pharmacy and the like. An administrator can be any medical professional such as a doctor, pharmacist, psychiatrist and the like, as well as any staff (e.g, a receptionist, nurse, technician, etc.), who also can be considered medical professionals depending on usage, working on behalf thereof. Also, in at least one exemplary embodiment, the administrator can be an employee of a healthcare insurance company and the like. Moreover, in at least one embodiment, it is envisioned that the operator will be the patient or a person acting on behalf thereof (e.g., guardian or caregiver) who is not an administrator for a medical provider or health insurance company.

Before inputting data at step 304, an operator may have to log in at step 302 to gain access to the storage system through any login means known to one having ordinary skill in the art. For example, logging in can be effectuated by providing a username and password to securely access the storage system via a secured Internet connection as is well known in the art. Business logic can be used to determine the level of access granted to the operator.

Figure 4:
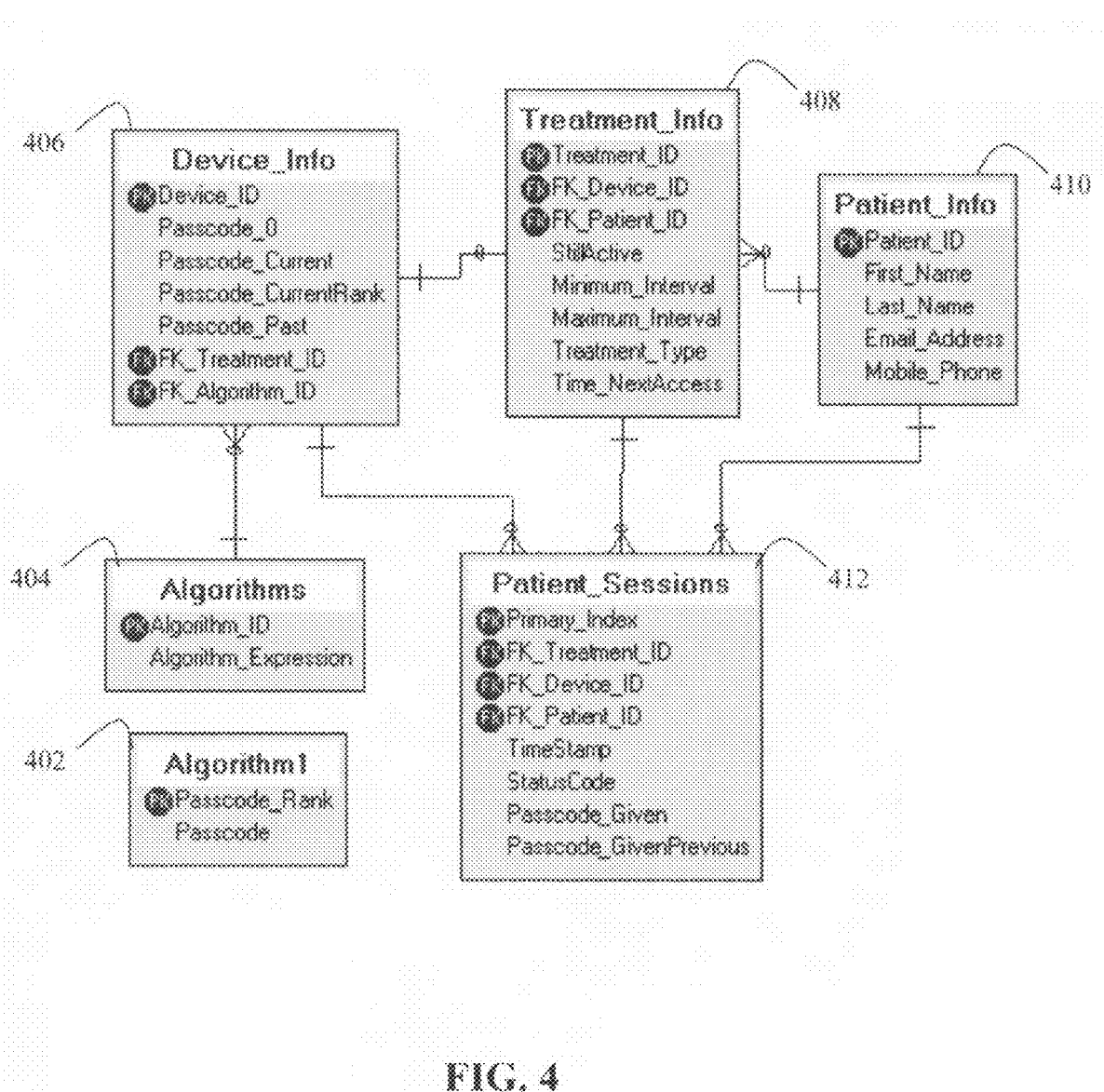
FIG. 4 is a database schema for an exemplary database implemented on a storage system.

At step 304, the operator can input data such as patient biographical data, device data including device identification data, medical/treatment data pertaining to patients and their prescribed medicament regimens and the like into the storage system, which can be stored and organized in a database (see, e.g., FIG. 4). As stated before, the storage system and any associated database can also include access authorization data and/or access authorization data algorithms for determining a limited-use access authorization data. The operator can input data via administrative screens for data entry such as webpage forms providing data entry means through GUI widgets.

For instance, during patient enrollment, the operator can enter needed patient biographical data, needed treatment/medical data including treatment regimen, the quantity of medicaments disposed within and housed by the dispensing device, dispensing device identification data (e.g., identification number) and the like known to one having ordinary skill in the art. Also, at this time, a patient can be provided with the medicament dispensing device as well as any needed information for contacting the interfacing system of an authorizing system (see, e.g., FIG. 2) in order to receive access authorization data such as a limited-use passcode for gaining access to a dosage of the medicaments.

For example, an exemplary code device for providing a web form for inputting data regarding a new dispensing device can include:

```
<?php
header("Content-type: text/html");
?>
<html>
    <head>
        <title>
Enter data to enroll a new device for the MedicaSafe system.
        </title>
    </head>
<?php
$db_host = "localhost";
$db_user = "root";
$db_pwd = "zbnm15";
$db_name = "db_ms1";
mysql_connect($db_host, $db_user, $db_pwd);
mysql_select_db($db_name);
?>
```

```
<body>
<?php
if (!isset ($_POST['submit'])) {
    ?>
    <form action="" method="post">
    Device ID Number: <input type="text" name="device_id"><br>
    Passcode 0: <input type="text" name="passcode_0"><br>
        Current Passcode: <input type="text"
        name="passcode_current"><br>
    Current Passcode Rank: <input type="text"
name="passcode_currentrank"><br>
    Algorithm ID: <input type="text" name="algorithm_id"><br>
    <input type="submit" name="submit" value="Submit!">
    </form>
    <?php
} else {
    $Device_ID = $_POST['device_id'];
    $Passcode_0 = $_POST['passcode_0'];
    $Passcode_Current = $_POST['passcode_current'];
    $Passcode_CurrentRank = $_POST['passcode_currentrank'];
    $Algorithm_ID = $_POST['algorithm_id'];
    $result=mysql_query("SELECT * FROM
Device_Info WHERE (Device_ID = '$Device_ID')");
    $number = mysql_num_rows($result);
    echo "$number";
    if ($number==0)
        {
        mysql_query("INSERT INTO Device_Info
            (Device_ID,Passcode_0,Passcode_Current,
            Passcode_CurrentRank,
            FK_Algorithm_ID) VALUES ('$Device_ID',
        '$Passcode_0','$Passcode_Current','$Passcode_CurrentRank',
    '$Algorithm_ID')");
            echo "Adding a new device....";
        }
    else
        {
        if (!mysql_query("
        UPDATE Device_Info SET
        Passcode_0='$Passcode_0',
        Passcode_Current='$Passcode_Current',
        Passcode_CurrentRank='$Passcode_CurrentRank',
        FK_Algorithm_ID='$Algorithm_ID'
        WHERE Device_ID='$Device_ID'
        ")) { die(mysql_error( ));}
            echo "Overiding data for existing device....";
        }
    $result = mysql_query("SELECT * FROM Device_Info WHERE
(Device_ID='$Device_ID')");
    $temp_passcode = mysql_result($result, 0,Passcode_Current);
    echo "Data for a New Device $Device_ID has been added with
        current passcode $temp_passcode.";
}
?>
</body>
</html>
```

Additionally, an exemplary code device for providing a web form for inputting patient-related data (which could be further customized by one with ordinary skill in the art to include additional patient biographical data, treatment/medical data including certain treatment regimen data, the quantity of medicaments disposed within and housed by the dispensing device, dispensing device identification data and the like) can include:

```
<?php
header("Content-type: text/html");
?>
<html>
    <head>
        <title>
Enter data to enroll a new treatment regimen for the MedicaSafe system
        </title>
    </head>
```

```
<?php
include_once("lib/dbaccess.php");
$temp=db_ms1_connect( );
?>
<body>
<?php
if (!isset ($_POST['submit']))   {
        ?>
        <form action="" method="post">
        Patient_ID (leave blank if new patient): <input type="text"
name="patient_id"><br>
        First Name: <input type="text" name="first_name"><br>
        Last Name: <input type="text" name="last_name"><br>
        Mobile Phone: <input type="text" name="mobile_phone"><br>
        Email Address: <input type="text" name="email_address"><br>
        Device ID Number: <input type="integer" name="device_id"><br>
        [Optional]Past Passcode: <input type="text" name="passcode_past"><br>
        [Optional]Treatment Type: <input type="text"
name="treatment_type"><br>
        Minimum Interval(minutes): <input type="text"
name="minimum_interval"><br>
        Maximum Interval(minutes): <input type="text"
name="maximum_interval"><br>
        <br>
        <input type="submit" name="submit" value="Submit!">
        </form>
        <?php
        } else
{
$Patient_ID = $_POST['patient_id'];
$First_Name= $_POST['first_name'];
$Last_Name = $_POST['last_name'];
$Mobile_Phone = $_POST['mobile_phone'];
$Email_Address = $_POST['email_address'];
$Device_ID = $_POST['device_id'];
$Passcode_Past = $_POST['passcode_past'];
$Treatment_Type = $_POST['treatment_type'];
$Minimum_Interval = (60*($_POST['minimum_interval']));
$Maximum_Interval = (60*($_POST['maximum_interval']));
$StillActive = TRUE;
$query= "SELECT * FROM Device_Info WHERE (Device_ID = '$Device_ID')";
$result = mysql_query($query);
if (!mysql_num_rows($result))
{exit ( "There is no device registered with this Device ID number yet.");}
$Result = mysql_query("SELECT * FROM Patient_Info WHERE
First_Name='$First_Name' AND Last_Name ='$Last_Name'");
if ((mysql_num_rows($Result) ==0))   {
        mysql_query("INSERT INTO Patient_Info (First_Name, Last_Name,
        Mobile_Phone, Email_Address) VALUES ('$First_Name',
'$Last_Name','$Mobile_Phone','$Email_Address')");
        $query = "SELECT Patient_ID FROM Patient_Info WHERE
First_Name='$First_Name' AND Last_Name = '$Last_Name'";
        $result = mysql_query ($query);
        $Patient_ID = mysql_result($result,0,"Patient_ID");
        echo "A New Patient has been created with ID $Patient_ID.";
        }
        else
        {
        $query = "SELECT Patient_ID FROM Patient_Info WHERE
(First_Name='$First_Name' AND Last_Name = '$Last_Name')";
        $result = mysql_query ($query);
        $Patient_ID = mysql_result($result,0,"Patient_ID");
        $query = "UPDATE Patient_Info SET Mobile_Phone = '$Mobile_Phone',
                Email_Address='$Email_Address' WHERE (First_Name =
'$First_Name' AND Last_Name='$Last_Name')" ;
        mysql_query($query);
        echo "The patient already had a Patient_ID of $Patient_ID. Mobile
number and email address have been updated.";
        }
        $now=Time( );
        $query = "UPDATE Treatment_Info SET StillActive= '0'   WHERE
FK_Device_ID='$Device_ID'";
        mysql_query ($query);
        $query = "INSERT INTO Treatment_Info (FK_Device_ID,
FK_Patient_ID,StillActive, Minimum_Interval, Maximum_Interval,Treatment_Type,
Time_NextAccess)
        VALUES
```

```
('$Device_ID','$Patient_ID','$StillActive','$Minimum_Interval','$Maximum_Interval
', '$Treatment_Type','$now')";
        $result = mysql_query ($query);
        $query = "SELECT * FROM Treatment_Info
        WHERE (FK_Patient_ID='$Patient_ID' AND FK_Device_ID = '$Device_ID' AND
StillActive = '1')";
        $result = mysql_query ($query);
        $Treatment_ID = mysql_result($result,0,"Treatment_ID");
        echo "The treatment information has been inserted with Treatment ID of
$Treatment_ID.";
mysql_close( );
}
?>
</body>
</html>
```

Still referring to FIG. 3, at step 306, the storage system (medical master system) can have business logic stored thereon configured to process the data (e.g., device and patient identification data, device status data, medical/treatment data, access authorization data, etc.) stored on the storage system in various ways as will also be appreciated by one having ordinary skill in the art. For example, the storage system can use the business logic to generate reports and output such reports at step 308, which can be displayed, downloaded and/or printed by the operator. The reports can include a variety of information including information directed to when the patient sought access to the dispensing device and presumably took a dosage of medicaments dispensed therefrom. These reports can be used by medical professionals to determine compliance with the treatment regimen and, thus, make decisions regarding the prescribed treatment, as well as investigate any indicia of addiction, abuse, misuse and the like.

At step 308, alerts can also be outputted (as previously discussed in conjunction with FIG. 2) to the patient, a caretaker, a medical professional and the like. These alerts can be of any type known to one having ordinary skill in the art including, for example, alerts transmitted through phone calls, text messages, emails and audible and/or visual alarms.

Now referring to FIG. 4, which is an exemplary database schema illustrating the structural aspects of an exemplary database that can be implemented on a server and form a storage system in accordance with at least one exemplary embodiment of the present invention. FIG. 4 has the following relation variables ("relvars"): Algorithm1 402; Algorithms 404; Device_Info 406; Treatment_Info 408; Patient_Info 410; and Patient_Sessions 412. As shown, each relvar has particular attributes where "PK" indicates that the attribute is a primary key and "FK" indicates that the attribute is a foreign key. The other attributes are candidate keys. Note that this database structure is but one of many possible database structures that one with ordinary skill in the art could conceive of for storing data related to the dispensing devices, patients, treatment regimens, device status, inferred information about the times and quantity of medicament dispensing, etc.

Figure 5:
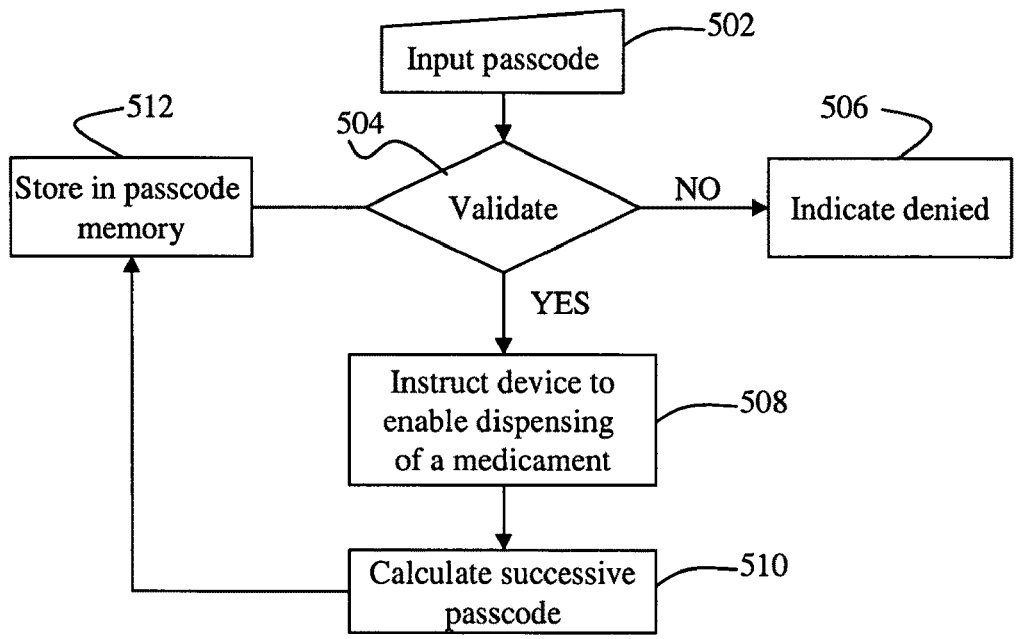
FIG. 5 is a flowchart showing an exemplary process for processing access authorization data by a medicament dispensing device.

Referring to FIG. 5, a process for enabling a medicament dispensing device to dispense a medicament in response to entering access authorization data is shown in accordance with at least one exemplary embodiment of the present invention. The dispensing device can house medicaments and provide a dosage thereof in response to inputting a validated access authorization data. The dispensing device can be constructed so as to be secure when access authorization data has not been provided, as it is necessary to prevent any sidestepping of the access authorization process. Thus, for example, the dispensing device may be securely sealed and tamper-resistant, and can enable or deny access to the medicaments based on the access authorization data communicated to the drug dispensing device by the user.

Notably, it is not necessary that the dispensing device be connected to a network at any time. In particular, it does not necessarily need to be networked with either the interfacing system or the storage system. The dispensing device can also independently compute and/or store current or subsequent access authorization data periodically and respond to enable or deny access based on current limited-use access authorization data being inputted. Thus, embodiments of the present invention such as IVR embodiments may not depend on a patient having Internet access, which may not be available to a patient for any of a variety of reasons.

Exemplary dispensing devices for use in conjunction with the process shown in FIG. 5 can include memory means such as various types of read only memory ("ROM") for storing instructions and data and processing means such as a central processing unit ("CPU") for processing data. Also, the exemplary dispensing device can include input means such as a keypad, voice recognition system, touch screen, camera, wireless reader, and the like for inputting access authorization data, including all input mechanisms known to one having ordinary skill in the art. Moreover, exemplary dispensing devices can include means such as a display, playable audio files and the like for relaying information to an operator of the dispensing device, including all output system known to one having ordinary skill in the art. Exemplary dispensing devices can be designed that track the quantity of medicaments contained therein and the times at which the patient seeks access to those medicaments. The device can also implement logic that constrains access to the medicaments to a certain limit of use (e.g., no more than three doses within a 48 hour period). Exemplary devices can also display information reflecting medicament access times, either in an encoded format or in format readable by a human.

Still referring to FIG. 5, at step 502, a patient (or a person acting on behalf thereof) can input limited-use access authorization data such as a single-use passcode, which may have been obtained from an authorizing system as described herein in conjunction with the process of FIG. 2. Once the access authorization data is inputted at step 502, the dispensing device can validate the access authorization data at step 504. For example, the CPU can compare the access authorization data inputted to a stored passcode and determine if they match. If the inputted access authorization data does not match and, thus, is invalid/denied, then the dispensing device can indicate such via the display (or by like means) at step 506. For example, the dispensing device can display: "No Match"; "Invalid"; "Access Denied"; "Denied"; and the like.

If the inputted access authorization data does match and is therefore validated, the CPU can instruct the dispensing device to enable a dosage of a medicament to be dispensed at step 508. At step 510, subsequent limited-use access authorization data such as the next single-use passcode can be computed based upon an algorithm or any random number generator known to one having ordinary skill in the art.

As one non-limiting example, an algorithm can make use of an initial five or seven digit number that is stored in an access number register such as memory forming part of a control mechanism such as a microcontroller. The first four digits of the five or seven digit number can be used as the initial single-use passcode to enable a medicament dispensing device. After which, the five or seven digit number can be multiplied by a random prime number that can also be stored in the access number register. The last seven or five numbers of the multiplication product can then be stored in the access number register. The first four digits of the multiplication product can be the next single-use passcode. As will be appreciated by one having skill in the art, successive single-use passcodes can thus be calculated ad infinitum. Such exemplary algorithms can produce seemingly random single-use passcodes. Table 1 below is a list of seemingly random single-use passcodes used as the passcodes for at least one exemplary embodiment.

TABLE 1

| Iteration | 5-digit product |
|---|---|
| 1 | 23566 |
| 2 | 44334 |
| 3 | 33222 |
| 4 | 46211 |
| 5 | 22344 |
| 6 | 25446 |
| 7 | 32154 |
| 8 | 25442 |
| 9 | 51224 |
| 10 | 46165 |
| 11 | 32452 |
| 12 | 64352 |
| 13 | 55433 |
| 14 | 16325 |
| 15 | 34314 |
| 16 | 52254 |
| 17 | 24544 |
| 18 | 26152 |
| 19 | 43162 |
| 20 | 42153 |
| 21 | 13266 |
| 22 | 44422 |
| 23 | 26525 |
| 24 | 24151 |
| 25 | 56136 |
| 26 | 34531 |
| 27 | 61534 |
| 28 | 36212 |
| 29 | 36452 |
| 30 | 64562 |
| 31 | 55136 |
| 32 | 32364 |
| 33 | 34313 |
| 34 | 51145 |
| 35 | 13655 |
| 36 | 31561 |
| 37 | 22341 |
| 38 | 31311 |
| 39 | 34661 |
| 40 | 64413 |
| 41 | 63466 |
| 42 | 52464 |
| 43 | 61642 |

TABLE 1-continued

| Iteration | 5-digit product |
|---|---|
| 44 | 36226 |
| 45 | 26561 |
| 46 | 31231 |
| 47 | 42215 |
| 48 | 11634 |
| 49 | 14362 |
| 50 | 25565 |

Still referring to FIG. 5, at step 512, the access authorization data computed at step 510 such as the next single-use passcode can be both stored in the memory of the dispensing device and stored in the storage system accessed by the interfacing server. Alternatively, an algorithm can be used to calculate and determine the next passcode, and the same algorithm should be used by both the interfacing server and the dispensing device to determine the next limited-use access authorization data. Also alternatively, both the device and the interfacing server can have access to separate but identical lists of valid access authorization data.

The limited-use access authorization data can be transmitted to a patient (or person acting on behalf thereof) by the interfacing system in conjunction with a storage system (medical master system). Importantly, the use of the same algorithm or same tables of access authorization data can allow independent calculation and storage of each limited-use access authorization data on both the dispensing device and the exemplary authorizing system of FIG. 2. Thus, it is not necessary that the dispensing device be networked with a storage system because it can have independent processing and storage capabilities for independently determining access authorization data.

In regard to access authorization data generation, particularly single-use passcode generation in accordance with at least one exemplary embodiment, single-use passcodes can be set to change at any desired time, which may occur periodically and/or frequently. As stated above, at the dispensing device level, a microcontroller, as one non-limiting example, can programmatically change the passcode to following a list of known passcodes, or in accordance with a random number generator such as an algorithm for such a purpose. In general, one with ordinary skill in the art can conceive of a variety of ways to implement a changing series or limited-use access authorization data, and ensure that the same list of limited-use access authorization data can be simultaneously computable at both the drug dispensing device and at the interfacing server.

Alternatively, singularly or in conjunction, the microcontroller can ensure that access authorization data is used for only a certain quantity of medicaments, or access to medicaments over a certain period of time, or a combination of quantity and time frame (e.g., a passcode works for up to three uses during the next twenty-four hours, and thereafter the passcode expires). Also, the microcontroller can track the times at which medicaments are accessed, store that information in memory, and consolidate that information into a status code which encodes information about the access history. It is possible to make this status code visible on a device display screen, for example in response to the pressing of certain keys on the key pad, and this device status data can be communicated during the interaction between the user and the interfacing server, such that device status data can be communicated to the interfacing server medical master system.

In at least one exemplary embodiment in which the limit of access is single use, the microcontroller can ensure that the access authorization data is used only once and is, thus, truly single-use. For example, it can invalidate entered access authorization data after one use even if it would be still valid under a designated time period but for the access authorization data being inputted. Thus, multiple doses could not be dispensed over the designated period of time. The interfacing and storage systems can also be configured in parallel (i.e. reproduce the process used by the dispensing device) so as to be able to provide the current and correct access authorization data, if available, when requested by a patient (or person acting on behalf thereof).

In at least one exemplary embodiment, an access authorization data reset mechanism can be provided to address any situations where the dispensing device and authorizing system (i.e. interfacing and storage systems) become out of sync or otherwise need resetting. The reset mechanism may function so as to reset the dispensing device to an initial or otherwise determinable state where the access authorization data may be known or determined.

Also, in exemplary embodiments, two or more sets of access authorization data such as two or more single-use passcodes may be enabled or active during overlapping times. For example, if a first passcode is set to expire shortly after a patient contacts the authorizing system (e.g., a minute), then it may be desirable that the system provide the patient with a second passcode that is not set to expire until a later time (e.g., ten minutes) so that the patient has additional and/or sufficient time to access the needed dosage. As another example, the first passcode could enable access to at most three medicaments over the course of twelve hours, whereas an alternative passcode could enable access to at most four medicaments over the course of twenty-four hours. The interfacing server, in conjunction with the storage system, can follow an algorithm that enables that server to selectively communicate one or none of the valid passcodes, depending on whether it is deemed medically advisable.

Figure 6:
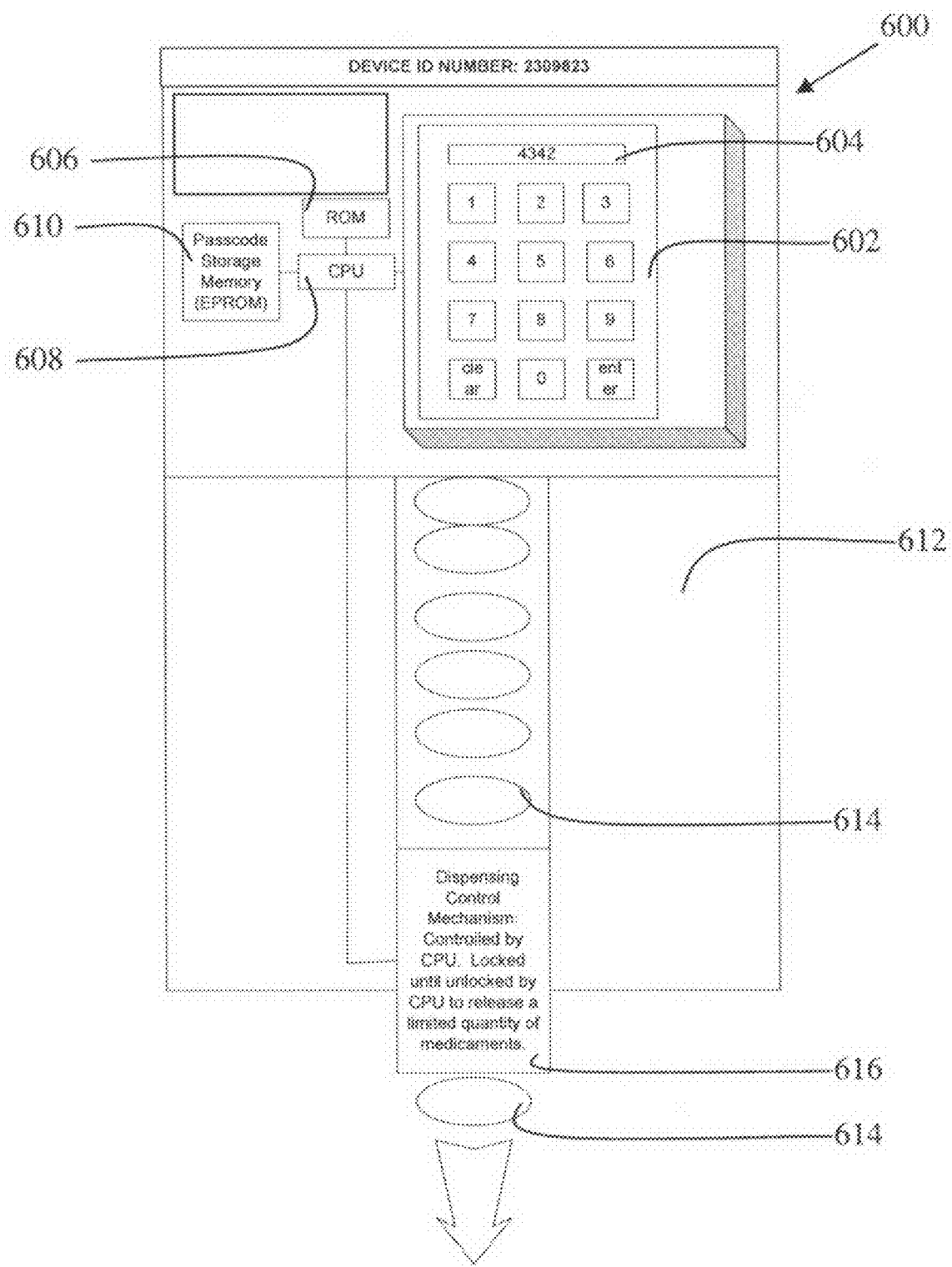
FIG. 6 is a figure showing an exemplary embodiment of a medicament dispensing device.
Figure 7:
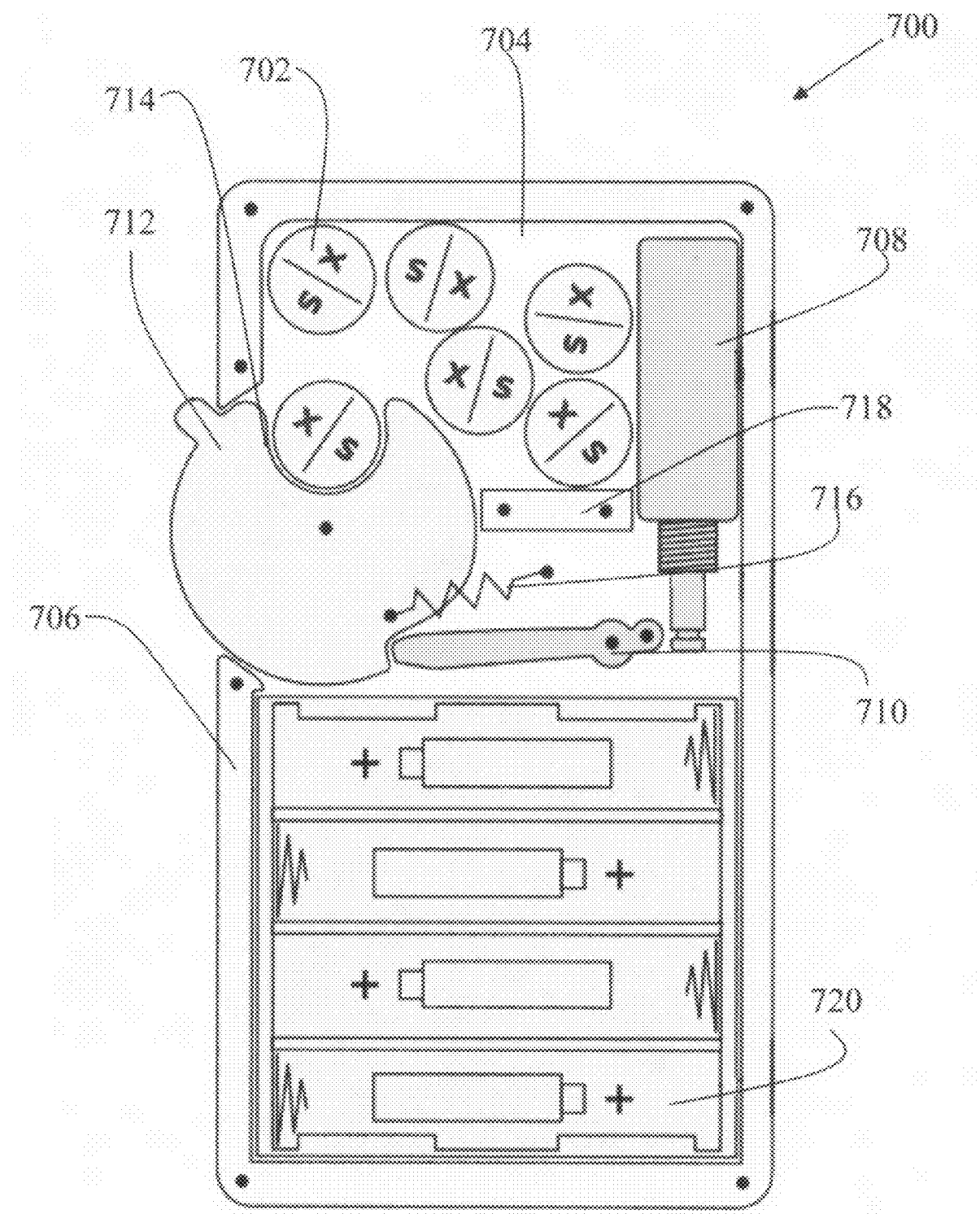
FIG. 7 is a figure showing another exemplary embodiment of a medicament dispensing device in a non-dispensing state.
Figure 8:
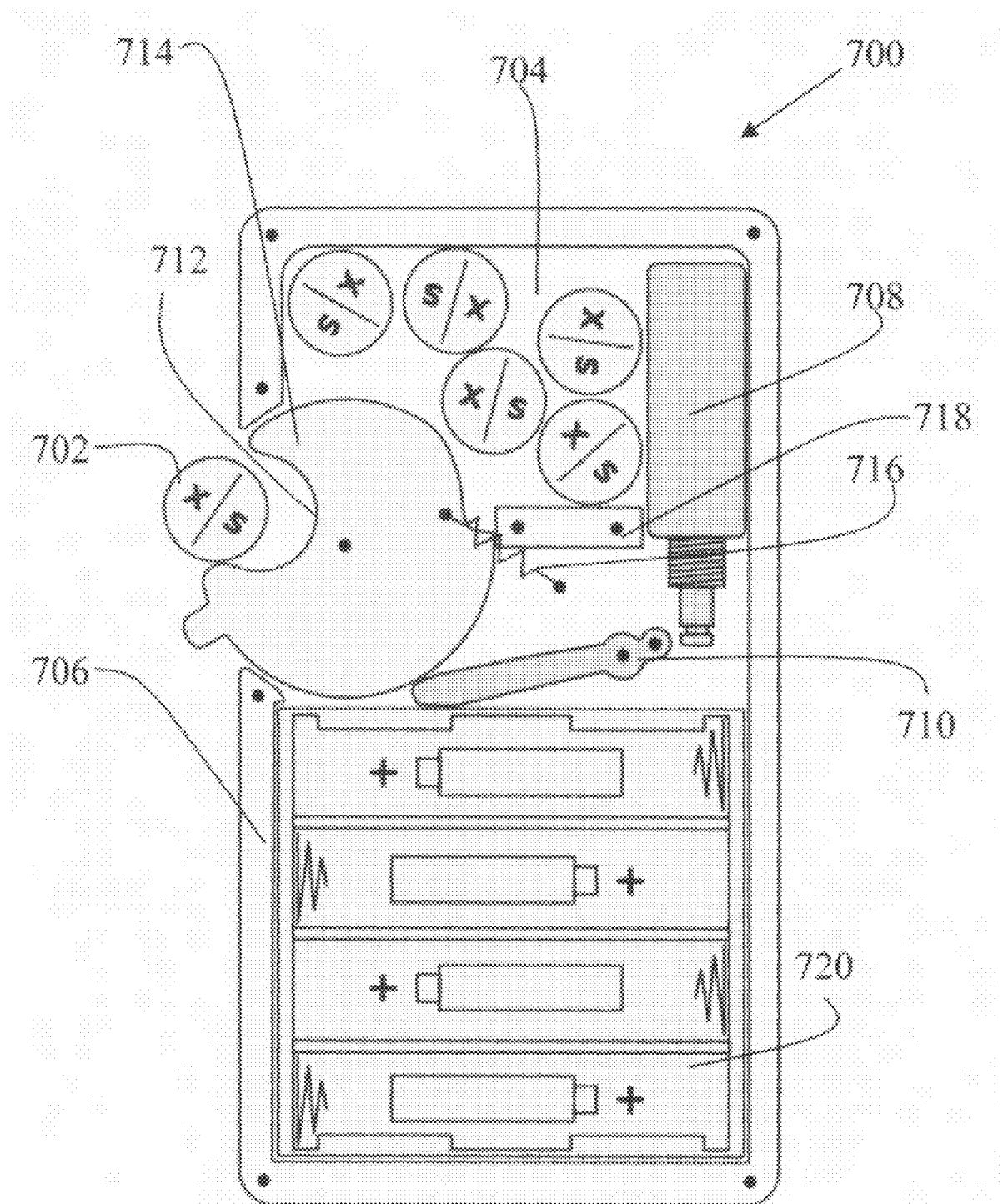
FIG. 8 is a figure showing the medicament dispensing device of FIG. 7 in a dispensing state.

FIGS. 6-8 generally show aspects and configurations for medicament dispensing devices in accordance with at least one exemplary embodiment of the present invention. Exemplary dispensing devices can dispense a dosage of medicaments without providing a patient with insecure access to all medicaments housed in the dispensing device. Dispensing devices can include control mechanisms that enable or disable dispensing activities, or, alternatively singularly or in conjunction, unlock or lock the dispensing devices. Further, exemplary embodiments may be capable of being connected to outside systems and sources, such as those that can be provided through the Internet via wired or wireless connections, although this is not a necessary feature in other exemplary embodiments as previously discussed.

Referring to FIG. 6, exemplary dispensing device 600 includes keypad 602 and display 604. Dispensing device 600 can also include CPU 608 that is operatively connected to main memory 606 such as ROM and passcode storage memory 610. For example, passcode storage memory 610 can be in the form of EPROM. Moreover, dispensing device 600 can include dispensing mechanism 612 for housing medicaments 614 where a medicament 614 can be dispensed by dispensing control mechanism 616 under the direction of CPU 608. In at least one exemplary embodiment, ROM 606 can primarily store instructions and data needed by CPU 608 for the operation of display 604 and dispensing control mechanism 616 as well as for generally validating and computing access authorization data (e.g., the needed algorithm data). While passcode storage memory 610 can primarily be directed to storing passcode data needed by the CPU 608 for validating inputted passcodes and computing subsequent passcodes.

Referring to FIGS. 7 and 8, another exemplary dispensing device is schematically depicted in accordance with at least one exemplary embodiment of the present invention. In FIG. 7, dispensing device 700 is in a locked/disengaged state where medicaments 702 can be securely housed in compartment 706 of housing 704. In at least one exemplary embodiment, the housing 704 of device 700 has a height of about 4.40 inches (vertical length as shown in FIG. 7) and a width of about 2.41 inches (horizontal length as shown in FIG. 7). In other embodiments, housing 704 can have any other suitable dimensions as will be appreciated by one having ordinary skill in the art.

As shown, solenoid 708, which is in a de-energized state, can be operatively associated with lever 710. In turn, lever 710 can be operatively associated with dispensing wheel 712. A holding niche 714 for capturing a dosage of medicaments 702 can be defined in dispensing wheel 712. Spring 716 can be attached to dispensing wheel 712 and be proximate lower boundary 718 of compartment 706.

Electronics package 720 can include control electronics including a processor (e.g., a CPU) and memory means, a power source such as batteries, user interface electronics for providing functionality to a user interface (e.g., a keypad/display) and the like known to one having ordinary skill in the art. The processor of electronics package 720 can be operatively connected to solenoid 708 for energizing solenoid 708.

Upon validation of an access authorization data, a processor can energize solenoid 708 effectuating the engaged state as shown in FIG. 8. The engaged (unlocked) state is effectuated through solenoid 708 (powered by the processor) cooperating with lever 710 that, in turn, cooperates to unlock dispensing wheel 712 such that a patient can manually turn the wheel and dispense a dosage of medicaments 702.

For example, an exemplary code device for enabling a dispensing device to accept input of access authorization data, validate that data and provide a signal output to enable the dispensing device to provide access to medicaments, and thereafter require a new passcode to enable further access to medicaments can include the exemplary code device below:

```
//*****************************************
// MedicaSafe Prototype Firmware v. 01
// (c) MedicaSafe, Inc.
// Contact: zeveland@gmail.com
// Target uC: ATMEGA168
//
//      a - 6/4/07 - created
//*****************************************
#define MEDICASAFE
// --v-- Includes --v--
#include "global.h"          //global settings
#include <avr/interrupt.h>   //interrupt support
#include <avr/eeprom.h>      //internal EEPROM handling routines (for
reading tile ID)
#include "timerx8.h"         //timer library
```

```
#include "medicasafe_helper.h"
// --^-- End Includes --^--
// --v-- Function Prototypes --v--
u08 check_code(void);
// --^-- End Function Prototypes --^--
// --v-- Seven-Segment Messages Defins --v--
#define HELLO_MESSAGE    1
#define OPEN_MESSAGE     2
#define ERROR_MESSAGE    3
#define RESET_MESSAGE    4
// --^-- End Seven-Segment Messages Defines --^--
// --v-- Global Variables --v--
u08 g_next_key;
u32 loop_count = 0;
u08 entered_code[6] = {'b', 'b', 'b', 'b', 'b', 'b'};
// --^-- End Global Variables --^--
int main(void) {
        // --v-- Configure the Ports --v--
        // DDRD, PORTD:
        //   7 - output, low (anode 2)
        //     6 - output, low (anode 4)
        //   5 - output, low (anode 1)
        //   4 - output, low (solenoid)
        //   3 - input, pullup (switch 8)
        //   2 - input, pullup (switch 2)
        //   1 - input, pullup (switch 1)
        //   0 - input, pullup (switch 4)
        //       DDRD: b7-0 - ooooiiii - 11110000 - 0xF0
        //           PORTD: b7-0 - llllpppp - 00001111 - 0x0F
        outb(DDRD, 0xF0);
        outb(PORTD, 0x0F);
        // DDRC, PORTC:
        //   7 - input, pullup (nc)
        //     6 - input, pullup (nc)
        //   5 - input, pullup (switch 7)
        //   4 - input, pullup (switch 5)
        //   3 - input, pullup (switch 6)
        //   2 - input, pullup (switch 3)
        //   1 - output, high (disp oe#)
        //   0 - output, low (disp le)
        //       DDRC: b7-0 - iiiiiioo - 00000011 - 0x03
        //           PORTC: b7-0 - pppppphl - 11111110 - 0xFE
        outb(DDRC, 0x03);
        outb(PORTC, 0xFE);
        // DDRB, PORTB:
        //   7 - input, no pullup (xtal)
        //     6 - input, no pullup (xtal)
        //   5 - output, low (disp clk)
        //   4 - input, pullup (nc)
        //   3 - output, low (disp sdi)
        //   2 - output, low (anode 6)
        //   1 - output, low (anode 3)
        //   0 - output, low (anode 5)
        //       DDRB: b7-0 - iioioooo - 00101111 - 0x2F
        //           PORTB: b7-0 - nnlpllll - 00010000 - 0x10
        outb(DDRB, 0x2F);
        outb(PORTB, 0x10);
        // --^-- End Port Configuration --^--
        // --v-- Startup Tasks --v--
        timerInit( );
        delay_ms(500);
        while (eeprom_is_ready( ) != 1) {
        }
        delay_ms(500);
        g_next_key = eeprom_read_byte(0x00);
        while ((g_next_key == 0x00) || (g_next_key == 0xFF)) {
                g_next_key = eeprom_read_byte(0x00);
                u08 i;
                for (i=0; i<255; i++) {
                        display_message(ERROR_MESSAGE);
                }
                turn_off_all_anodes( );
                delay_ms(1000);
        }
        u08 j;
        for (j=0; j<100; j++) {
                display_message(HELLO_MESSAGE);
        }
        // --^-- End Startup Tasks --^--
        // --v-- Program Variables --v--
```

```
            u08 current_code_digit = 0;
            u08 prev_sw_state = 0;
            u08 active_key;
            u08 key_down_registered;
            u08 key_down_loop_count;
            #define key_down_thresh 1
            // --^-- End Program Variables --^--
            // --v-- Begin Main Program Loop --v--
            while (1) {
                    u08 current_sw_state = return_switch_states( );
                    if ((current_sw_state == 0) && (prev_sw_state == 0)) {
                    } else if ((prev_sw_state == 0) && (current_sw_state != 0)) {
                            u08 i;
                            for (i=0; i<8; i++) {
                                    if (current_sw_state & (0x01 << i)) {
                                            active_key = i+1;
                                    }
                            }
                            key_down_registered = 0;
                            key_down_loop_count = loop_count;
                    } else if ((prev_sw_state == current_sw_state) &&
(current_sw_state != 0)) {
                            if ((key_down_registered == 0) && (loop_count −
key_down_loop_count > key_down_thresh)) {
                                    if (active_key < 7) {
                                            entered_code[current_code_digit] = active_key;
                                            entered_code[current_code_digit + 1] = 'u';
                                            current_code_digit++;
                                    } else if ((active_key == 7) && (current_code_digit
== 0)) {
                                            u08 current_code = eeprom_read_byte(0x00);
                                            u08 buf[6] = {'b', 'b', 'b', 'b',
current_code/10, current_code%10};
                                            u08 i;
                                            for (i=0; i<100; i++) {
                                                    display_string(buf);
                                            }
                                    } else if ((active_key == 7) && (current_code_digit >
0)) {
                                            entered_code[current_code_digit] = 'b';
                                            entered_code[current_code_digit − 1] = 'u';
                                            current_code_digit−−;
                                    } else if ((active_key == 8) && (entered_code[0] !=
'b')) {
                                            u08 check_code_result = check_code( );
                                            if (check_code_result == 0) {
                                                    current_code_digit = 0;
                                            }
                                    } else if ((active_key == 8) && (entered_code[0] ==
'b')) {
                                            entered_code[0] = 'u';
                                    }
                                    key_down_registered = 1;
                            }
                    }
                    display_string(entered_code);
                    prev_sw_state = current_sw_state;
                    loop_count++;
                    /*
                    u08 eeprom_byte = eeprom_read_byte(0x02);
                    display_number(1, eeprom_byte);
                    delay_ms(1);
                    eeprom_byte = eeprom_read_byte(0x03);
                    display_number(2, eeprom_byte);
                    delay_ms(1);
                    eeprom_byte = eeprom_read_byte(0x04);
                    display_number(3, eeprom_byte);
                    delay_ms(1);
                    eeprom_byte = eeprom_read_byte(0x05);
                    display_number(4, eeprom_byte);
                    delay_ms(1);
                    eeprom_byte = eeprom_read_byte(0x06);
                    display_number(5, eeprom_byte);
                    delay_ms(1);
                    */
            }
            // --^-- End Main Program Loop --^--
}
// --v-- Subroutines --v--
u08 check_code(void) {
```

```
            u08 i;
            if ((entered_code[0] == 6) && (entered_code[1] == 6) &&
(entered_code[2] == 6) && (entered_code[3] == 6) && (entered_code[4] == 6) &&
(entered_code[5] == 6)) {
                    for (i=0; i<200; i++) {
                            display_message(RESET_MESSAGE);
                    }
                    eeprom_write_byte(0x00, 1);
                    for (i=0; i<6; i++) {
                            entered_code[i] = 'b';
                    }
                    return 0;
            }
            while (eeprom_is_ready( ) != 1) {
            }
            delay_ms(5);
            u08 current_code = eeprom_read_byte(0x00);
            u08 eeprom_offset = (6 * (current_code−1)) + 2;
            for (i=0; i<5; i++) {
                    while (eeprom_is_ready( ) != 1) {
                    }
                    delay_ms(5);
                    u08 eeprom_code_byte = eeprom_read_byte(i + eeprom_offset);
                    if (eeprom_code_byte != entered_code[i]) {
                            return 1;
                    }
            }
            for (i=0; i<50; i++) {
                    display_message(OPEN_MESSAGE);
            }
            turn_off_all_anodes( );
            for (i=0; i<100; i++) {
                    activate_solenoid( );
                    delay_ms(50);
                    deactivate_solenoid( );
                    delay_ms(5);
            }
// for (i=0; i<255; i++) {
//         display_string(eeprom_code_bytes);
//     }
            for (i=0; i<6; i++) {
                    entered_code[i] = 'b';
            }
            if (current_code == 50) {
                    eeprom_write_byte(0x00, 1);
            } else {
                    eeprom_write_byte(0x00, current_code+1);
            }
            return 0;
}
// -- -- End Subroutines --^--
#ifndef MEDICASAFE_HELPER_H_
#define MEDICASAFE_HELPER_H_
#include "global.h"
u08 get_switch_press(void);
u08 return_switch_states(void);
void display_string(u08* string_to_display);
void display_message(u08 message_number);
void show_screen(u08* pdata);
void display_number(u08 seven_seg_number, u08 number_to_display);
void display_character (u08 seven_seg_number, u08 character_unpacked);
void cycle_display_clock(u08 clock_cycles);
void turn_off_all_anodes(void);
void turn_on_anode(u08 anode);
void turn_off_anode(u08 anode);
void activate_solenoid(void);
void deactivate_solenoid(void);
#endif /*MEDICASAFE_HELPER_H_*/
#include <avr/io.h>                              //IO definitions (port names,
pin names, etc.)
#include <stdlib.h>
#include "global.h"                              //global settings
#include "timerx8.h"
#include "medicasafe_helper.h"
// --v-- Switch Routines --v--
u08 get_switch_press(void) {
            u08 switch_press = 0;
            u08 first_switch_state = return_switch_states( );
            delay_ms(10);
            u08 second_switch_state = return_switch_states( );
```

```
                if (first_switch_state == second_switch_state) {
                        if (first_switch_state == 0x01)         switch_press = 1;
                        if (first_switch_state == 0x02)         switch_press = 2;
                        if (first_switch_state == 0x04)         switch_press = 3;
                        if (first_switch_state == 0x08)         switch_press = 4;
                        if (first_switch_state == 0x10)         switch_press = 5;
                        if (first_switch_state == 0x20)         switch_press = 6;
                        if (first_switch_state == 0x40)         switch_press = 7;
                        if (first_switch_state == 0x80)         switch_press = 8;
                }
                return switch_press;
}
u08 return_switch_states(void) {
        u08 data = 0;
        if (bit_is_clear(SW1_PORT, SW1_PIN))     data |= 0x01;
        if (bit_is_clear(SW2_PORT, SW2_PIN))     data |= 0x02;
        if (bit_is_clear(SW3_PORT, SW3_PIN))     data |= 0x04;
        if (bit_is_clear(SW4_PORT, SW4_PIN))     data |= 0x08;
        if (bit_is_clear(SW5_PORT, SW5_PIN))     data |= 0x10;
        if (bit_is_clear(SW6_PORT, SW6_PIN))     data |= 0x20;
        if (bit_is_clear(SW7_PORT, SW7_PIN))     data |= 0x40;
        if (bit_is_clear(SW8_PORT, SW8_PIN))     data |= 0x80;
        return data;
}
// -- -- End Switch Routines -- --
// --v-- Seven Segment Patterns --v--
// 0x90 is '9' on both - after that:
//      0xFF, 0xFF - blank
//      ??, 0x40 - underscore
u08 number_segments_all_but_last[10] = {0xEE, 0x28, 0xCD, 0x6D, 0x2B, 0x67,
0xE7, 0x2C, 0xEF, 0x6F};
u08 number_segments_last[10] = {0x77, 0x41, 0x3B, 0x6B, 0x4D, 0x6E, 0x7E,
0x43, 0x7F, 0x6F};
#define HELLO_MESSAGE   1
#define OPEN_MESSAGE    2
#define ERROR_MESSAGE   3
#define RESET_MESSAGE   4
//u08 hello_segments[6] = {0x11, 0x54, 0x34, 0x3D, 0x11};
u08 hello_segments[6] = {0xAB, 0xC7, 0xC2, 0xC2, 0xEE, 0x00};
u08 open_segments[6] = {0xEE, 0x8F, 0xC7, 0xA1, 0x00, 0x00};
u08 error_segments[6] = {0xC7, 0x81, 0x81, 0xE1, 0x81, 0x00};
u08 reset_segments[6] = {0x81, 0xC7, 0x67, 0xC7, 0x29, 0x00};
// -- -- End Seven Segment Patterns -- --
// --v-- High-Level Display Routines --v--
void display_message(u08 message_number) {
        if (message_number == HELLO_MESSAGE) {
                show_screen(hello_segments);
        }
        if (message_number == OPEN_MESSAGE) {
                show_screen(open_segments);
        }
        if (message_number == ERROR_MESSAGE) {
                show_screen(error_segments);
        }
        if (message_number == RESET_MESSAGE) {
                show_screen(reset_segments);
        }
}
void display_string(u08* string_to_display) {
        u08 i;
        u08 unpacked_characters[6];
        for (i=0; i<6; i++) {
                if (string_to_display[i] < 10) {
                        display_number(i, string_to_display[i]);
                } else if (string_to_display[i] == 'u') {
                        if (i < 5) {
                                display_character(i, 0x40);
                        } else {
                                display_character(i, 0x20);
                        }
                } else if (string_to_display[i] == 'b') {
                        display_character(i, 0x00);
                }
                delay_ms(1);
        }
}
void show_screen(u08* pdata) {
        u08 i;
        for (i=0; i<6; i++) {
                display_character(i, pdata[i]);
```

```
                delay_ms(1);
        }
}
// --^-- End High-Level Display Routines --^--
// --v-- Low-Level Display Routines --v--
void display_number(u08 seven_seg_number, u08 number_to_display) {
        if (seven_seg_number != 5)
                display_character(seven_seg_number,
number_segments_all_but_last[number_to_display]);
        else
                display_character(seven_seg_number,
number_segments_last[number_to_display]);
}
void display_character(u08 seven_seg_number, u08 character_unpacked) {
        u08 i;
        turn_off_all_anodes( );
        DISP_OE_PORT |= _BV(DISP_OE_PIN);      // de-assert OE (active-low):
        DISP_LE_PORT &= ~_BV(DISP_LE_PIN);     // de-assert LE (active-high):
        for (i=0; i<8; i++) {
                if (bit_is_set(character_unpacked, i))
                        DISP_SDI_PORT |= _BV(DISP_SDI_PIN);
                else
                        DISP_SDI_PORT &= ~_BV(DISP_SDI_PIN);
                cycle_display_clock(1);
        }
        DISP_LE_PORT |= _BV(DISP_LE_PIN);
        delay(10);
        DISP_LE_PORT &= ~_BV(DISP_LE_PIN);
        delay(10);
        DISP_OE_PORT &= ~_BV(DISP_OE_PIN);
        delay(10);
        cycle_display_clock(2);
        turn_on_anode(seven_seg_number);
}
void cycle_display_clock(u08 clock_cycles) {
        u08 i;
        for (i=0; i<clock_cycles; i++) {
                DISP_CLK_PORT |= _BV(DISP_CLK_PIN);
                delay(10);
                DISP_CLK_PORT &= ~_BV(DISP_CLK_PIN);
                delay(10);
        }
}
// --^-- End Low-Level Display Routines --^--
// --v-- Display Anode Control Routines --v--
void turn_off_all_anodes(void) {
        ANODE1_PORT &= ~_BV(ANODE1_PIN);
        ANODE2_PORT &= ~_BV(ANODE2_PIN);
        ANODE3_PORT &= ~_BV(ANODE3_PIN);
        ANODE4_PORT &= ~_BV(ANODE4_PIN);
        ANODE5_PORT &= ~_BV(ANODE5_PIN);
        ANODE6_PORT &= ~_BV(ANODE6_PIN);
}
void turn_on_anode (u08 anode) {
        if (anode == 0)     ANODE1_PORT |= _BV(ANODE1_PIN);
        if (anode == 1)     ANODE4_PORT |= _BV(ANODE4_PIN);
        if (anode == 2)     ANODE2_PORT |= _BV(ANODE2_PIN);
        if (anode == 3)     ANODE5_PORT |= _BV(ANODE5_PIN);
        if (anode == 4)     ANODE3_PORT |= _BV(ANODE3_PIN);
        if (anode == 5)     ANODE6_PORT |= _BV(ANODE6_PIN);
}
void turn_off_anode(u08 anode) {
        if (anode == 0)     ANODE1_PORT &= ~_BV(ANODE1_PIN);
        if (anode == 1)     ANODE4_PORT &= ~_BV(ANODE4_PIN);
        if (anode == 2)     ANODE2_PORT &= ~_BV(ANODE2_PIN);
        if (anode == 3)     ANODE5_PORT &= ~_BV(ANODE5_PIN);
        if (anode == 4)     ANODE3_PORT &= ~_BV(ANODE3_PIN);
        if (anode == 5)     ANODE6_PORT &= ~_BV(ANODE6_PIN);
}
// --^-- End Display Anode Control Routines --^--
// --v-- Solenoid Control Routines --v--
void activate_solenoid(void) {
        SOLENOID_PORT |= _BV(SOLENOID_PIN);
}
void deactivate_solenoid(void) {
        SOLENOID_PORT &= ~_BV(SOLENOID_PIN);
}
// --^-- End Solenoid Control Routines --^--
```

In at least one other exemplary embodiment, an administrator such as a nurse can respond to requests for access authorization data from a patient (or a person acting on behalf thereof). A patient may use a communicative intermediary to contact the administrator. For example, it is contemplated that the administrator can be a nurse employed by a call center for receiving requests for access authorization data. Also, a patient can place a phone call that an administrator can receive, initiate a web-based correspondence with an administrator, transmit a text message viewable by an administrator and the like for requesting access authorization data. A patient can also correspond face-to-face with an administrator if such an option is available.

In such exemplary embodiments, the patient can provide identifying data to the administrator. As will be appreciated by one having ordinary skill in the art, access authorization data can be authorized and/or determined through an administrator operating a computing device or be accomplished manually or a combination of the two. As one non-limiting example, the administrator can operate a computing device capable of authorizing and providing an access authorization data. Alternatively, an administrator can view the medication regimen and a patient's access history and authorize an access authentication data. As described above, the access authorization data can be used by a patient to access a dosage of medicaments from a dispensing device. Also, the access authorization can be limited-use access authorization data.

The administrator can communicate the access authorization data, if appropriate, to the patient via, for example, a communicative intermediary. Thus, an administrator may communicate the access authorization data over a telephone, through the Internet, via a responsive text message and the like known to one having ordinary skill in the art.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A system for access to medicaments comprising:
   an interfacing system configured to interface with a communications intermediary;
   a portable dispensing device for dispensing the medicaments, the dispensing device being capable of providing limited access to the medicaments in response to valid access authorization data, the access authorization data independently computable by both the dispensing device and the interfacing system and being of limited use, and the dispensing device being capable of being easily transported by a user,
   whereby limited access to the medicaments is granted via communication of the valid limited-use authorization data from the interfacing system to a user via the communications intermediary.

2. The system of claim 1 wherein the interfacing system includes a web server and the communicative intermediary includes a client computing device having web capabilities.

3. The system of claim 1 wherein the interfacing system includes an interactive voice response (IVR) system and the communicative intermediary includes a telephonic device having telephone capabilities.

4. The system of claim 1 wherein the access authorization data includes one of a passcode, a password and a visual ticket.

5. The system of claim 1 wherein the access authorization data no longer provides access to the medicaments after a certain limit of use, the limit of use including one of a predetermined amount of usage, a predetermined period of time and a predetermined amount of usage during a predetermined amount of time.

6. The system of claim 1 wherein the dispensing device and the interfacing system are separately capable of computing and updating the valid limited-use authorization data using one of computational calculation according to an algorithm and retrieving the information from a data storage system.

7. The system of claim 1 wherein the interfacing system is interfaced with a data storage system populated by a plurality of data including one of dispensing device entries, information about prescribed treatment and information about users.

8. The system of claim 1 wherein the interfacing system compiles data about when the user is or is not seeking access to the medicaments and generates for interested persons an output including one of reports and alerts,
   whereby it is possible to approximately monitor overuse and underuse of the medicaments.

9. The system of claim 1 wherein more than one access authorization data are valid at the dispensing device at any one time, each access authorization data has different limits of use, and the choice of which access authorization data to communicate to the user allows remote control of the rules for access to the medicaments in the device.

10. The system of claim 1 wherein the interfacing system includes one of a live person interface and a computer, and the communicative intermediary includes one of a face-to-face conversation and a known communication technology,
    whereby the interfacing system includes one of an automated system and a manually operated system.

11. The system of claim 1 wherein valid identifying data is communicated by a user to the interfacing system before valid access authorization data is communicated to the user from said interfacing system,
    whereby additional relevant information is gathered before granting access to said medicaments, said additional information including at least one of user identity, user symptoms, device status, treatment status, and medicament usage information.

12. The method of claim 11 wherein the identifying data includes one of device identification information identifying the dispensing device, identification information identifying the prescribed treatment regimen, treatment information, information describing the patient, device information in the form of a status code indicating the pattern of medicament dispensing, patient symptoms, patient activity, device activity, and medicament usage information.

13. The system of claim 11 wherein data derived from at least one of identifying data and the times when the user is provided with limited-use access authorization data is used to generate an output including one of a report and an alert.

14. A medicament dispensing device comprising:
   a portable dispensing unit containing a locking unit, such that the dispensing unit can be locked or unlocked and capable of dispensing medicaments only when unlocked,
   the dispensing unit being capable of being easily transported by a user,
   the dispensing unit also including an input evaluation unit capable of accepting input data from a user, and capable of signaling the locking system to unlock when the input data is determined to be valid, the dispensing unit also including a monitoring unit capable of monitoring dispensing of medicaments, and capable of signaling said locking unit to lock when dispensing has reached a certain limit of use associated with said valid input data, whereby the device can be selectively unlocked and medicaments accessed only when the user provides valid input data, the medicaments being provided up to a certain limit of use associated with said input data.

15. The system of claim 14 wherein the access authorization data includes one of a passcode, a password and a visual ticket.

16. The system of claim 14 wherein the access authorization data no longer provides access to the medicaments after a certain limit of use, the limit including one of a predetermined amount of usage, a predetermined period of time and a predetermined amount of usage during a predetermined amount of time.

17. The system of claim 14 wherein more than one limited-use access authorization data are valid at the dispensing device at any one time, each limited-use access authorization data has different limits of use, and the choice of which access authorization data to communicate to the user allows remote control of the rules for access to the medicaments in the device.

18. The system of claim 14 wherein communication to the user of the access authorization information and communication by the user of any information necessary to receive said access authorization data occurs via one of a telephone, web interface, and a personal communication device.

19. The system of claim 14 wherein valid identifying data is communicated by a user before valid limited-use access authorization data is communicated to the user in return, whereby it is possible to gather additional relevant information before granting access to said medicaments said additional relevant information including one of, user identity, user symptoms, device status, treatment status, medicament usage information.

20. The system of claim 19 wherein the identifying data includes one of device identification information identifying the dispensing device, identification information identifying the prescribed treatment regimen, treatment information, information describing the patient, device information including a status code indicating the pattern of medicament dispensing, patient symptoms, patient activity, device activity, and medicament usage information.

21. The system of claim 19 wherein data derived from one of identifying data and the times when the user seeks access to the limited-use access authorization is used to generate an output including one of a report and an alert.

22. A method of enabling medicament access for a user comprising:

receiving identifying data from the user;

evaluating whether or not to provide access authorization data for medicaments stored in a portable device based on the identifying data received and if a decision is made to grant access, then;

determining said access authorization data, wherein the access authorization data enables dispensing the medicaments from the portable device up to a limit of use, and communicating the access authorization data to the user.

23. The method of claim 22 wherein communication with the user occurs via one of a telephonic device, a computing device, a text-messaging device, and a face-to-face conversation.

24. The method of claim 22 wherein the access authorization data includes one of a passcode, a password, a data transmission, and a visual ticket.

25. The method of claim 22 wherein the access authorization data no longer provides normal access to the medicaments after a certain limit of use, the limit being one of a predetermined amount of usage, a predetermined period of time and a predetermined amount of usage during a predetermined amount of time.

26. The method of claim 22 wherein both the portable device and the evaluating entity responsible for communicating the access authorization data to the user are in agreement on valid authorization data using one of computational calculation according to an algorithm, retrieving information from a data storage system, or having the authorization data preset in hardware.

27. The method of claim 22 wherein more than one access authorization data are valid at the portable device at any one time, each access authorization data is associated with different limits of use, and the choice of which access authorization data to communicate to the user allows remotely controlling the level of access that the user has to the medicaments.

28. The method of claim 22 wherein the session for communicating with the user to collect identifying data also includes communication of questions to the user, whereby the communication session can be used to gather and record medically relevant information about a patient, including at least one of medical symptoms, activities, behaviors, attitudes, the dispensing history of the dispensing device, the times at which the user seeks access to medicaments, the effectiveness of the medicaments, issues related to medicament adherence, and issues related to health outcomes.

29. The method of claim 22 wherein the portable device generates a status code which reflects information about the dispensing of medicaments from the portable device, and this status code can be communicated by the user as part of identifying data, whereby communication of this status code by the user relays information about the user's behavior in accessing medicaments from the portable device.

30. The method of claim 22 wherein the identifying data includes one of information identifying the portable device, information describing the device, device activity, device status, device information including a status code indicating the pattern of medicament dispensing, information identifying the prescribed treatment regimen, treatment information, information identifying the patient, patient symptoms, patient activity, and medicament usage information.

31. The method of claim 22 wherein data about dispensing, as derived from one of identifying data and the times when the user seeks access authorization, is used to generate one of reports, alerts, and notifications to one or more interested persons, whereby others can be informed if the user is seeking access to the medicaments in a pattern that suggests lack of adherence to a prescribed treatment regimen.

32. The method of claim 22 wherein data derived from one of identifying data and the times when the user receives access authorization data is used to generate outputs including one of a report and an alert.

* * * * *